US010350137B2

(12) United States Patent
Lurie et al.

(10) Patent No.: US 10,350,137 B2
(45) Date of Patent: Jul. 16, 2019

(54) ELEVATION TIMING SYSTEMS AND METHODS FOR HEAD UP CPR

(71) Applicant: Keith G. Lurie, Minneapolis, MN (US)

(72) Inventors: Keith G. Lurie, Minneapolis, MN (US); Kanchana Sanjaya Gunesekera Karunaratne, Escondido, CA (US); Joseph Manno, La Jolla, CA (US); John P. Grimm, Santee, CA (US); Casimir A. Sienkiewicz, Minneapolis, MN (US); Robert R. Roberts, III, Saint Paul, MN (US)

(73) Assignee: Keith G. Lurie, Minneapolis, MN (US)

( * ) Notice: Subject to any disclaimer, the term of this patent is extended or adjusted under 35 U.S.C. 154(b) by 219 days.

(21) Appl. No.: 15/601,494

(22) Filed: May 22, 2017

(65) Prior Publication Data

US 2017/0258677 A1  Sep. 14, 2017
US 2019/0159962 A9  May 30, 2019

Related U.S. Application Data

(63) Continuation-in-part of application No. 15/285,063, filed on Oct. 4, 2016, which is a continuation-in-part
(Continued)

(51) Int. Cl.
*A61H 31/00* (2006.01)
*A61G 13/12* (2006.01)
(Continued)

(52) U.S. Cl.
CPC ......... *A61H 31/004* (2013.01); *A61G 13/121* (2013.01); *A61G 13/122* (2013.01);
(Continued)

(58) Field of Classification Search
CPC . A61M 16/0048; A61H 31/00; A61H 31/008; A61H 31/004–007; A61H 31/02;
(Continued)

(56) References Cited

U.S. PATENT DOCUMENTS 1,995,583 A    3/1935 Sanderson
3,461,858 A    8/1969 Michaelson
(Continued)

FOREIGN PATENT DOCUMENTS

EP    2289477 A1    9/2014
EP    3107516 A2    12/2016
(Continued)

OTHER PUBLICATIONS

U.S. Appl. No. 15/133,967, filed Apr. 20, 2016, Final Office Action dated Mar. 13, 2017, all pages.
(Continued)

*Primary Examiner* — LaToya M Louis
(74) *Attorney, Agent, or Firm* — Kilpatrick Townsend & Stockton LLP

(57) ABSTRACT

A method for performing cardiopulmonary resuscitation (CPR) includes elevating the head, heart and shoulders of an individual from a starting elevation angle to a final elevation angle greater than zero degrees relative to horizontal while performing CPR by repeatedly compressing the chest. The method includes elevating the brain within a time period selected to be slow enough to permit a sufficient amount of blood to flow to the brain throughout the elevation time period. The method also includes regulating the intrathoracic pressure of the individual while performing CPR. The performance of chest compressions is stopped and after stopping the performance of chest compressions, the head, heart, and shoulders are promptly from the final elevation angle within a timeframe selected to prevent significant
(Continued)

drainage of blood from the brain until the head, heart and shoulders are lowered.

17 Claims, 26 Drawing Sheets

Related U.S. Application Data of application No. 15/160,492, filed on May 20, 2016, which is a continuation-in-part of application No. 15/133,967, filed on Apr. 20, 2016, now Pat. No. 9,801,782, which is a continuation-in-part of application No. 14/996,147, filed on Jan. 14, 2016, now Pat. No. 9,750,661, which is a continuation-in-part of application No. 14/935,262, filed on Nov. 6, 2015, now Pat. No. 9,707,152, which is a continuation-in-part of application No. 14/677,562, filed on Apr. 2, 2015, now Pat. No. 10,092,481, which is a continuation of application No. 14/626,770, filed on Feb. 19, 2015, now Pat. No. 10,245,209.

(60) Provisional application No. 61/941,670, filed on Feb. 19, 2014, provisional application No. 62/000,836, filed on May 20, 2014, provisional application No. 62/087,717, filed on Dec. 4, 2014, provisional application No. 62/242,655, filed on Oct. 16, 2015.

(51) Int. Cl.
*A61N 1/39* (2006.01)
*A61G 13/04* (2006.01)

(52) U.S. Cl.
CPC .......... *A61H 31/005* (2013.01); *A61H 31/006* (2013.01); *A61H 31/007* (2013.01); *A61H 31/008* (2013.01); *A61N 1/39* (2013.01); *A61G 13/04* (2013.01); *A61H 2201/0176* (2013.01); *A61H 2201/0188* (2013.01); *A61H 2201/0192* (2013.01); *A61H 2201/1207* (2013.01); *A61H 2201/1409* (2013.01); *A61H 2201/1604* (2013.01); *A61H 2201/1609* (2013.01); *A61H 2201/1623* (2013.01); *A61H 2201/1676* (2013.01); *A61H 2201/50* (2013.01); *A61H 2201/5043* (2013.01); *A61H 2201/5061* (2013.01); *A61H 2201/5097* (2013.01); *A61H 2203/0456* (2013.01); *A61H 2230/04* (2013.01); *A61H 2230/06* (2013.01); *A61H 2230/10* (2013.01); *A61H 2230/208* (2013.01); *A61H 2230/305* (2013.01)

(58) Field of Classification Search
CPC ........ A61H 2031/001; A61H 2031/002; A61H 2031/003; A61H 2031/025
See application file for complete search history.

(56) References Cited

U.S. PATENT DOCUMENTS

| | | |
|---|---|---|
| 3,509,899 A | 5/1970 | Hewson |
| 3,804,082 A | 4/1974 | Tarjan et al. |
| 3,866,604 A | 2/1975 | Curless |
| 3,870,038 A | 3/1975 | Arblaster |
| 3,985,126 A | 10/1976 | Baralow |
| 4,060,079 A | 11/1977 | Reinhold, Jr. |
| 4,095,590 A | 6/1978 | Harrigan |
| 4,168,554 A | 9/1979 | Hindes |
| 4,194,732 A | 3/1980 | Liebman |
| 4,362,336 A | 12/1982 | Zapf et al. |
| 4,534,075 A | 8/1985 | Schnitzler |
| 4,915,095 A | 4/1990 | Chun |
| 5,048,136 A | 9/1991 | Popitz |
| 5,316,907 A | 5/1994 | Lurie |
| 5,399,148 A | 3/1995 | Waide et al. |
| 5,400,448 A | 3/1995 | Zwickey |
| 5,423,772 A | 6/1995 | Lurie |
| 5,454,779 A | 10/1995 | Lurie et al. |
| 5,487,722 A | 1/1996 | Sherman et al. |
| 5,490,820 A | 2/1996 | Schock et al. |
| 5,538,002 A | 7/1996 | Boussignac et al. |
| 5,549,581 A | 8/1996 | Lurie |
| 5,551,420 A | 9/1996 | Lurie et al. |
| 5,588,422 A | 12/1996 | Lurie |
| 5,618,665 A | 4/1997 | Lurie |
| 5,634,222 A | 6/1997 | Zwickey |
| 5,643,231 A | 7/1997 | Lurie |
| 5,645,522 A | 7/1997 | Lurie et al. |
| 5,692,498 A | 12/1997 | Lurie et al. |
| 5,722,963 A | 3/1998 | Lurie |
| 5,730,122 A | 3/1998 | Lurie |
| 5,730,136 A | 3/1998 | Laufer |
| 5,827,893 A | 10/1998 | Lurie |
| 5,919,210 A | 7/1999 | Lurie |
| 5,984,909 A | 11/1999 | Lurie |
| 6,001,085 A | 12/1999 | Lurie |
| 6,029,667 A | 2/2000 | Lurie |
| 6,062,219 A | 5/2000 | Lurie et al. |
| 6,078,834 A | 6/2000 | Lurie |
| 6,142,962 A | 11/2000 | Mollenauer |
| 6,155,257 A | 12/2000 | Lurie et al. |
| 6,224,562 B1 | 5/2001 | Lurie et al. |
| 6,234,916 B1 | 5/2001 | Carusillo et al. |
| 6,234,985 B1 | 5/2001 | Lurie et al. |
| 6,277,107 B1 | 8/2001 | Lurie |
| 6,312,399 B1 | 11/2001 | Lurie et al. |
| 6,357,065 B1 | 3/2002 | Adams |
| 6,371,119 B1 | 4/2002 | Zadini et al. |
| 6,425,393 B1 | 7/2002 | Lurie et al. |
| 6,446,288 B1 | 9/2002 | Pi |
| 6,446,962 B1 | 9/2002 | Pi |
| 6,459,933 B1 | 10/2002 | Lurie et al. |
| 6,463,327 B1 | 10/2002 | Lurie et al. |
| 6,486,206 B1 | 11/2002 | Lurie |
| 6,526,973 B1 | 3/2003 | Lurie et al. |
| 6,587,726 B2 | 7/2003 | Lurie et al. |
| 6,604,523 B2 | 8/2003 | Lurie et al. |
| 6,656,166 B2 | 12/2003 | Lurie |
| 6,751,818 B2 | 6/2004 | Troop |
| 6,776,156 B2 | 8/2004 | Lurie et al. |
| 6,863,656 B2 | 3/2005 | Lurie |
| 6,935,336 B2 | 8/2005 | Lurie et al. |
| 6,938,618 B2 | 9/2005 | Lurie et al. |
| 6,986,349 B2 | 1/2006 | Lurie |
| 7,044,128 B2 | 5/2006 | Lurie |
| 7,056,296 B2 | 6/2006 | Sherman et al. |
| 7,060,041 B1 | 6/2006 | Weil et al. |
| 7,082,945 B2 | 8/2006 | Lurie |
| 7,174,891 B2 | 2/2007 | Lurie et al. |
| 7,185,649 B2 | 3/2007 | Lurie |
| 7,195,012 B2 | 3/2007 | Lurie |
| 7,195,013 B2 | 3/2007 | Lurie |
| 7,204,251 B2 | 4/2007 | Lurie |
| 7,210,480 B2 | 5/2007 | Lurie et al. |
| 7,275,542 B2 | 10/2007 | Lurie et al. |
| 7,296,312 B2 | 11/2007 | Menkedick |
| 7,311,668 B2 | 12/2007 | Lurie et al. |
| 7,347,832 B2 | 3/2008 | Jensen et al. |
| 7,569,021 B2 | 8/2009 | Sebelius et al. |
| 7,682,312 B2 | 3/2010 | Lurie |
| 7,766,011 B2 | 8/2010 | Lurie |
| 7,836,881 B2 | 11/2010 | Lurie et al. |
| 7,899,526 B2 | 3/2011 | Benditt et al. |
| 8,011,367 B2 | 9/2011 | Lurie et al. |
| 8,151,790 B2 | 4/2012 | Lurie et al. |
| 8,210,176 B2 | 7/2012 | Metzger et al. |
| 8,291,534 B2 | 10/2012 | Karlson |
| 8,408,204 B2 | 4/2013 | Lurie |
| 8,690,807 B2 | 4/2014 | Hiebert |
| 8,702,633 B2 | 4/2014 | Voss et al. |
| 8,752,220 B2 | 6/2014 | Soderberg et al. |

(56) References Cited

U.S. PATENT DOCUMENTS

| | | |
|---|---|---|
| 8,755,902 B2 | 6/2014 | Lurie et al. |
| 8,763,610 B2 | 7/2014 | Schmidt |
| 8,967,144 B2 | 3/2015 | Lurie |
| 9,707,152 B2 | 7/2017 | Lurie et al. |
| 9,750,661 B2 | 9/2017 | Lurie et al. |
| 9,801,782 B2 | 10/2017 | Lurie et al. |
| 10,092,481 B2 | 10/2018 | Lurie |
| 2002/0002347 A1 | 1/2002 | Kelly et al. |
| 2002/0069878 A1 | 6/2002 | Lurie et al. |
| 2002/0170562 A1 | 11/2002 | Lurie et al. |
| 2003/0062040 A1 | 4/2003 | Lurie et al. |
| 2004/0016428 A9 | 1/2004 | Lurie |
| 2004/0058305 A1 | 3/2004 | Lurie et al. |
| 2004/0116840 A1 | 6/2004 | Cantrell et al. |
| 2004/0200474 A1 | 10/2004 | Lurie |
| 2004/0211415 A1 | 10/2004 | Lurie |
| 2004/0211416 A1 | 10/2004 | Lurie |
| 2004/0211417 A1 | 10/2004 | Lurie |
| 2004/0231664 A1 | 11/2004 | Lurie et al. |
| 2005/0165334 A1 | 7/2005 | Lurie |
| 2005/0199237 A1 | 9/2005 | Lurie |
| 2005/0217677 A1 | 10/2005 | Lurie et al. |
| 2005/0267381 A1 | 12/2005 | Benditt |
| 2006/0162077 A1 | 7/2006 | McDaniel et al. |
| 2006/0258964 A1 | 11/2006 | Biondo |
| 2006/0277683 A1 | 12/2006 | Lamire et al. |
| 2007/0021683 A1 | 1/2007 | Benditt et al. |
| 2007/0157385 A1 | 7/2007 | Lemire |
| 2007/0277826 A1 | 12/2007 | Lurie |
| 2008/0045867 A1 | 2/2008 | Jensen et al. |
| 2008/0047555 A1 | 2/2008 | Lurie et al. |
| 2008/0255482 A1 | 10/2008 | Lurie |
| 2009/0062701 A1 | 3/2009 | Yannopoulos et al. |
| 2009/0277447 A1 | 11/2009 | Voss et al. |
| 2009/0308400 A1 | 12/2009 | Wilson et al. |
| 2010/0031961 A1 | 2/2010 | Schmidt |
| 2010/0179442 A1 | 7/2010 | Lurie |
| 2010/0319691 A1 | 12/2010 | Lurie et al. |
| 2011/0030141 A1 | 2/2011 | Soderberg et al. |
| 2011/0047709 A1 | 3/2011 | Tarsaud et al. |
| 2011/0098612 A1 | 4/2011 | Lurie |
| 2011/0132377 A1 | 6/2011 | Phillips |
| 2011/0160782 A1 | 6/2011 | Lurie et al. |
| 2011/0201979 A1 | 8/2011 | Voss et al. |
| 2011/0297147 A1 | 12/2011 | Lick et al. |
| 2012/0016179 A1 | 1/2012 | Paradis et al. |
| 2012/0042881 A1 | 2/2012 | Paulussen et al. |
| 2012/0109027 A1 | 5/2012 | Gozelski et al. |
| 2012/0203147 A1 | 8/2012 | Lurie et al. |
| 2012/0260428 A1 | 10/2012 | Franklin |
| 2012/0266383 A1 | 10/2012 | Pi |
| 2012/0330199 A1 | 12/2012 | Lurie et al. |
| 2012/0330200 A1 | 12/2012 | Voss et al. |
| 2013/0231593 A1 | 9/2013 | Yannopoulos et al. |
| 2014/0005566 A1 | 1/2014 | Homuth et al. |
| 2014/0048061 A1 | 2/2014 | Yannopoulos et al. |
| 2014/0082842 A1 | 3/2014 | Jackson |
| 2014/0171839 A1 | 6/2014 | Fleming |
| 2014/0276269 A1 | 9/2014 | Illindala |
| 2014/0363391 A1 | 12/2014 | Yannopoulos et al. |
| 2015/0057580 A1 | 2/2015 | Illindala |
| 2015/0231026 A1 | 8/2015 | Lurie |
| 2015/0231027 A1 | 8/2015 | Lurie |
| 2016/0058660 A1 | 3/2016 | Lurie et al. |
| 2016/0128899 A1 | 5/2016 | Lurie et al. |
| 2016/0228326 A1 | 8/2016 | Lurie et al. |
| 2016/0338904 A1 | 11/2016 | Lurie et al. |
| 2016/0354271 A1 | 12/2016 | Evgenyevna et al. |
| 2017/0119622 A1 | 5/2017 | Lurie et al. |
| 2017/0258677 A1 | 9/2017 | Lurie et al. |
| 2018/0000687 A1 | 1/2018 | Lurie et al. |
| 2018/0008510 A1 | 1/2018 | Lurie et al. |
| 2018/0125749 A1 | 5/2018 | Lurie et al. |

FOREIGN PATENT DOCUMENTS

| | | |
|---|---|---|
| WO | 2015/124102 A2 | 8/2015 |
| WO | 2015127102 A2 | 11/2015 |
| WO | 2017066770 A1 | 4/2017 |

OTHER PUBLICATIONS

International Search Report and Written Opinion of PCT/US2016/057366 dated Mar. 13, 2017, all pages.

Advisory Action dated Jul. 11, 2016, for U.S. Appl. No. 14/677,562, 4 pages.

Debaty G, et al. "Tilting for perfusion: Head-up position during cardiopulmonary resuscitation improves brain flow in a porcine model of cardiac arrest." Resuscitation. 2015: 87: 38-43.

Final Office Action dated May 27, 2016, for U.S. Appl. No. 14/667,562, 9 pages.

International Preliminary Report on Patentability dated Sep. 1, 2016, for International Patent Application No. PCT/US2015/016651, all pages.

International Search Report and Written Opinion dated Jul. 8, 2015 for International Patent Application No. PCT/US2015/016651, all pages.

Lurie, Keith G. (2015) "The Physiology of Cardiopulmonary Resuscitation," Anesthesia & Analgesia, doi:10.1513/ANE.0000000000000926, in Ryu, et. al. "The Effect of Head Up Cardiopulmonary Resuscitation on Cerebral and Systemic Hemodynamics." Resuscitation. 2016: 102: 29-34.

Lurie, Keith G. "Mechanical Devices for cardiopulmonary resuscitation: an update," "Emergency Medicine Clinics of North America," Dec. 2002, vol. 20, Issue 4, pp. 771-784.

Non-Final Office Action dated Aug. 26, 2016, for U.S. Appl. No. 14/996,147, 15 pages.

Non-Final Office Action dated Jan. 6, 2016, for U.S. Appl. No. 14/677,562, 33 pages.

Non-Final Office Action dated Sep. 9, 2016, for U.S. Appl. No. 14/935,262, all pages.

Non-Final Office Action dated Sep. 6, 2016, for U.S. Appl. No. 14/677,562, 12 pages.

Notice of Publication dated Aug. 11, 2016, for U.S. Appl. No. 15/133,967.

Physio-Control Inc., "Lucas CPR," retrieved from http://www.lucas-cpr.com/en/lucas_cpr/lucas_cpr.

Voelckel et al "The effects of positive end-expiratory pressure during active compression decompression cardiopulmonary resuscitation with the inspiratory threshold valve." Anesthesia and Analgesia. Apr. 2001: 92(4): 967-74.

Zoll Medical Corporation, "The System for High-Quality CPR", 2015, all pages.

U.S. Appl. No. 14/677,562, filed Apr. 2, 2015, Non-Final Office Action dated Jun. 13, 2017, all pages.

U.S. Appl. No. 15/133,967, filed Apr. 20, 2016, Advisory Action dated Jun. 7, 2017, all pages.

U.S. Appl. No. 14/626,770, Non-Final Rejection dated Jun. 7, 2018, all pages.

U.S. Appl. No. 14/677,562, Final Rejection dated Jan. 23, 2018, all pages.

U.S. Appl. No. 14/677,562, Notice of Allowance dated Sep. 4, 2018, all pages.

U.S. Appl. No. 15/160,492, Final Rejection dated Aug. 9, 2018, all pages.

U.S. Appl. No. 15/285,063, Final Rejection dated May 11, 2018, all pages.

EP Patent Application No. 15751853.1 filed Feb. 19, 2015, Extended European Search Report dated Feb. 10, 2017, all pages.

"Lucas CPR", Chest Compression System, Physio Control, Available online at: http://www.lucas-cpr.com/en/lucas_cpr/lucas_cpr, Sep. 7, 2018, 16 pages.

"The System for High-Quality CPR", Zoll Medical Corporation, Available online at: https://www.zoll.com/medicaltechnology/ CPR, Accessed from internet on Sep. 11, 2018, 2 pages.

(56) References Cited

OTHER PUBLICATIONS

U.S. Appl. No. 14/677,562 received a Non-Final Office Action, dated Sep. 24, 2015, 12 pages.
U.S. Appl. No. 14/677,562 received a Notice of Allowance, dated Jul. 23, 2018, 10 pages.
U.S. Appl. No. 14/935,262 received a Restriction Requirement, dated Jun. 2, 2016, 7 pages.
U.S. Appl. No. 14/996,147 received a Restriction Requirement, dated Jul. 18, 2016, 7 pages.
U.S. Appl. No. 15/133,967 received a Non-Final Office Action, dated Oct. 11, 2016, 21 pages.
U.S. Appl. No. 15/133,967 received a Notice of Allowance, dated Jul. 5, 2017, 11 pages.
U.S. Appl. No. 15/160,492 received a Non-Final Office Action, dated Jan. 11, 2018, 15 pages.
EP15751853.1 received an Extended European Search Report, dated Oct. 2, 2017, 9 pages.
PCT/US2015/016651 received an Invitation to Pay Additional Fees and Partial Search Report, dated Apr. 27, 2015, 3 pages.
PCT/US2016/057366 received an Invitation to Pay Additional Fees and Partial Search Report, dated Dec. 12, 2016, 2 pages.
Voelckel et al., "The Effects of Positive End-Expiratory Pressure During Active Compression Decompression Cardiopulmonary Resuscitation with the Inspiratory Threshold Valve", Anesthesia and Analgesia, vol. 92, No. 4, Apr. 2001, pp. 967-974.
International Patent Application No. PCT/US2015/016651 received an International Preliminary Report on Patentability, dated Aug. 23, 2016, 10 pages.
U.S. Appl. No. 14/935,262 received a Notice of Allowance, dated Jan. 4, 2017, 16 pages.
U.S. Appl. No. 14/996,147 received a Notice of Allowance, dated Jan. 18, 2017, all pages.
U.S. Appl. No. 14/677,562 received a Final Office Action, dated Jan. 9, 2017, all pages.
International EP Patent Application No. 15751853.1 received an Extended European Search Report, dated Feb. 10, 2017, all pages.
U.S. Appl. No. 14/677,562 received a Final Office Action, dated Jan. 9, 2017, 19 pages.
U.S. Appl. No. 14/677,562 received a Notice of Allowance, dated Jul. 23, 2018, 13 pages.
U.S. Appl. No. 14/996,147 received a Notice of Allowance, dated Jan. 18, 2017, 17 pages.
U.S. Appl. No. 14/966,147 received a Non Final Office Action, dated Aug. 26, 2016, 15 pages.
U.S. Appl. No. 15/160,492 received a Final Rejection dated Aug. 9, 2018, all pages.
U.S. Appl. No. 14/626,770 received Non-Final Rejection dated Jun. 7, 2018, all pages.
PCT/US2016/057366 Application No. received an International Preliminary Report on Patentability, dated Apr. 17, 2018, all pages.
U.S. Appl. No. 14/935,262 received a Notice of Allowance dated Jan. 4, 2017, all pages.
Voelckel et al "The effects of positive end-25 expiratory pressure during active compression decompression cardiopulmonary resuscitation with the inspiratory threshold valve." Anesthesia and Analgesia. Apr. 2001: 92(4): 967-74.
Ryu, et al. "The Effect of Head Up Cardiopulmonary Resuscitation on Cerebral and Systemic Hemodynamics." Resuscitation. 2016: 102: 29-34. Print.
Khandelwal, et. al. "Head-Elevated Patient Positioning Decreases 25 Complications of Emergent Tracheal Intubation in the Ward and Intensive Care Unit." Anesthesia & Analgesia. Apr. 2016: 122: 1101-1107.
ISR/WO mailed on Jul. 8, 2015 for International Patent Application PCT/US2015/016651 filed on Feb. 19, 2015, all pages.
U.S. Appl. No. 15/285,063 received an Advisory Action, dated Dec. 20, 2018, 4 pages.
U.S. Appl. No. 14/626,770 received a Notice of Allowance, dated Dec. 14, 2018, 9 pages.
U.S. Appl. No. 15/160,492 received an Advisory Action, dated Dec. 3, 2018, 3 pages.
U.S. Appl. No. 15/160,492 received a Notice of Allowance, dated Dec. 13, 2018, 25 pages.

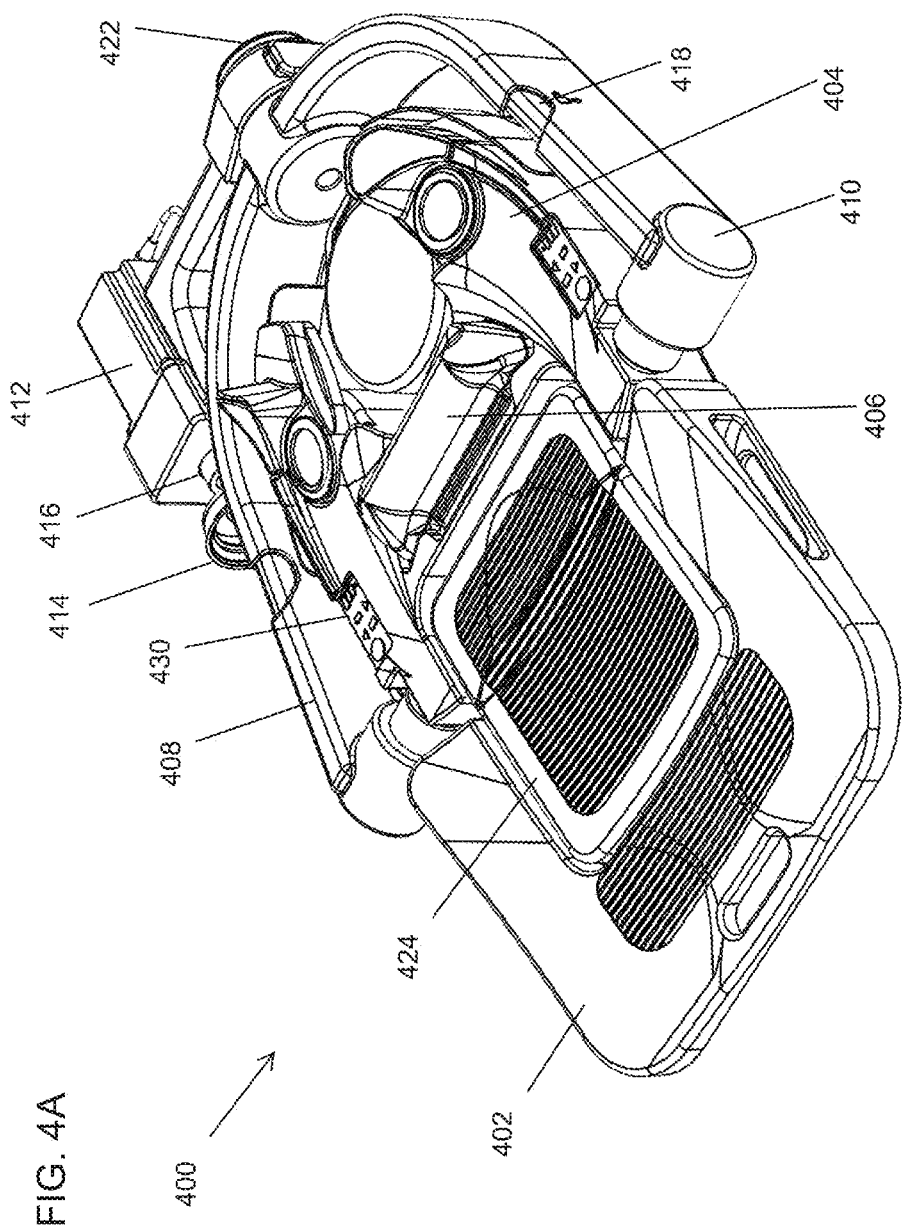

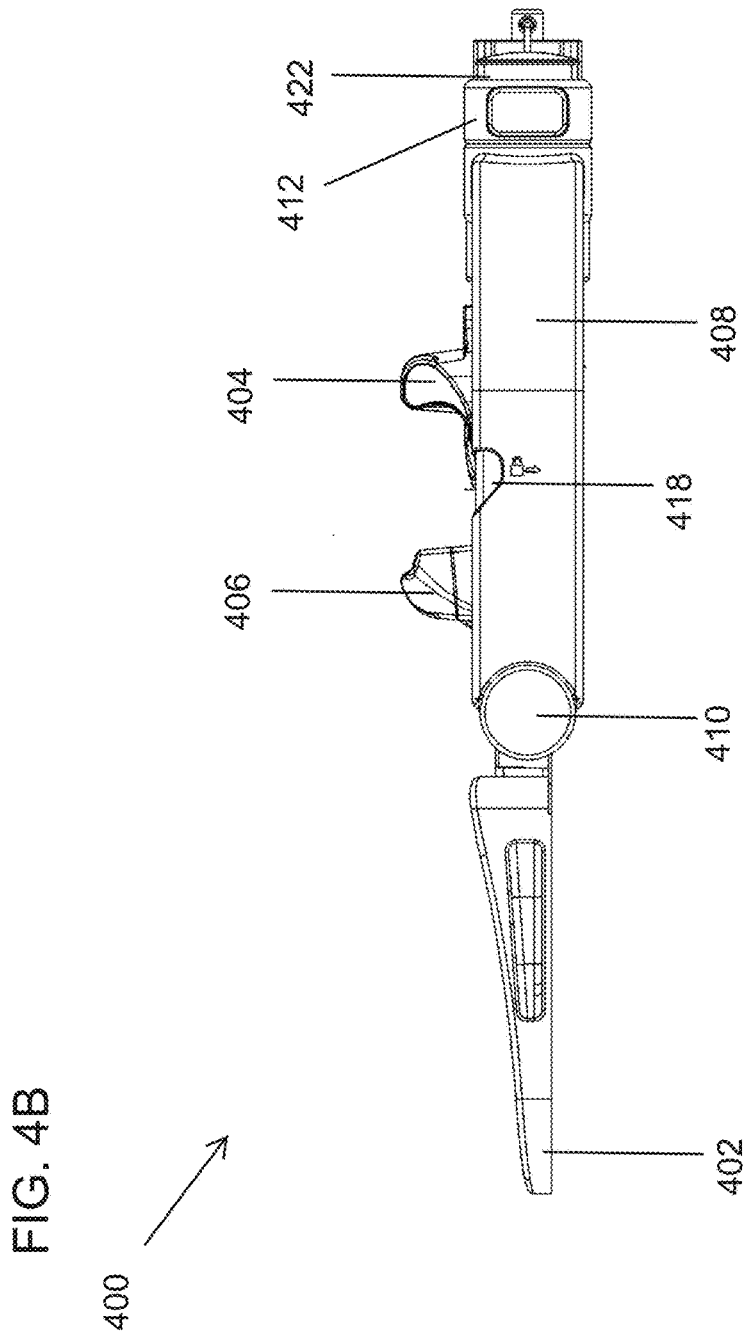

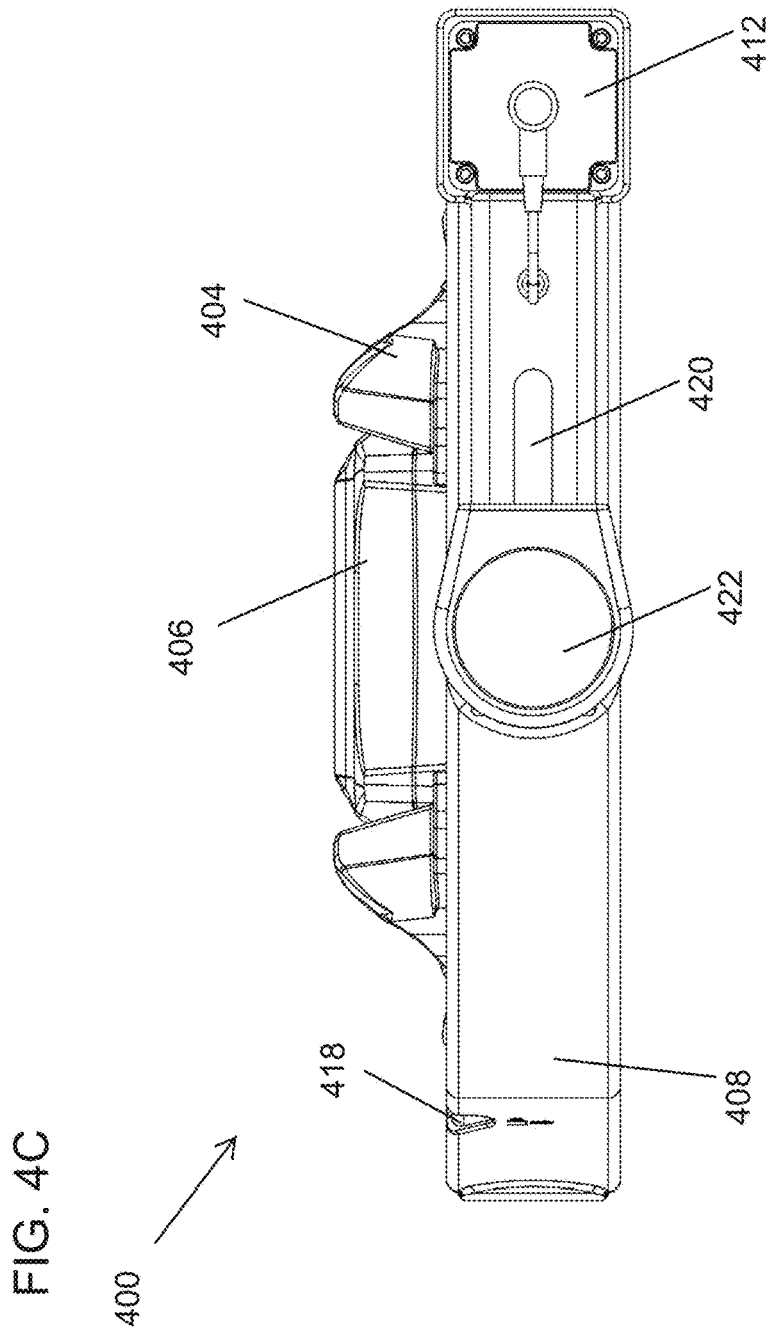

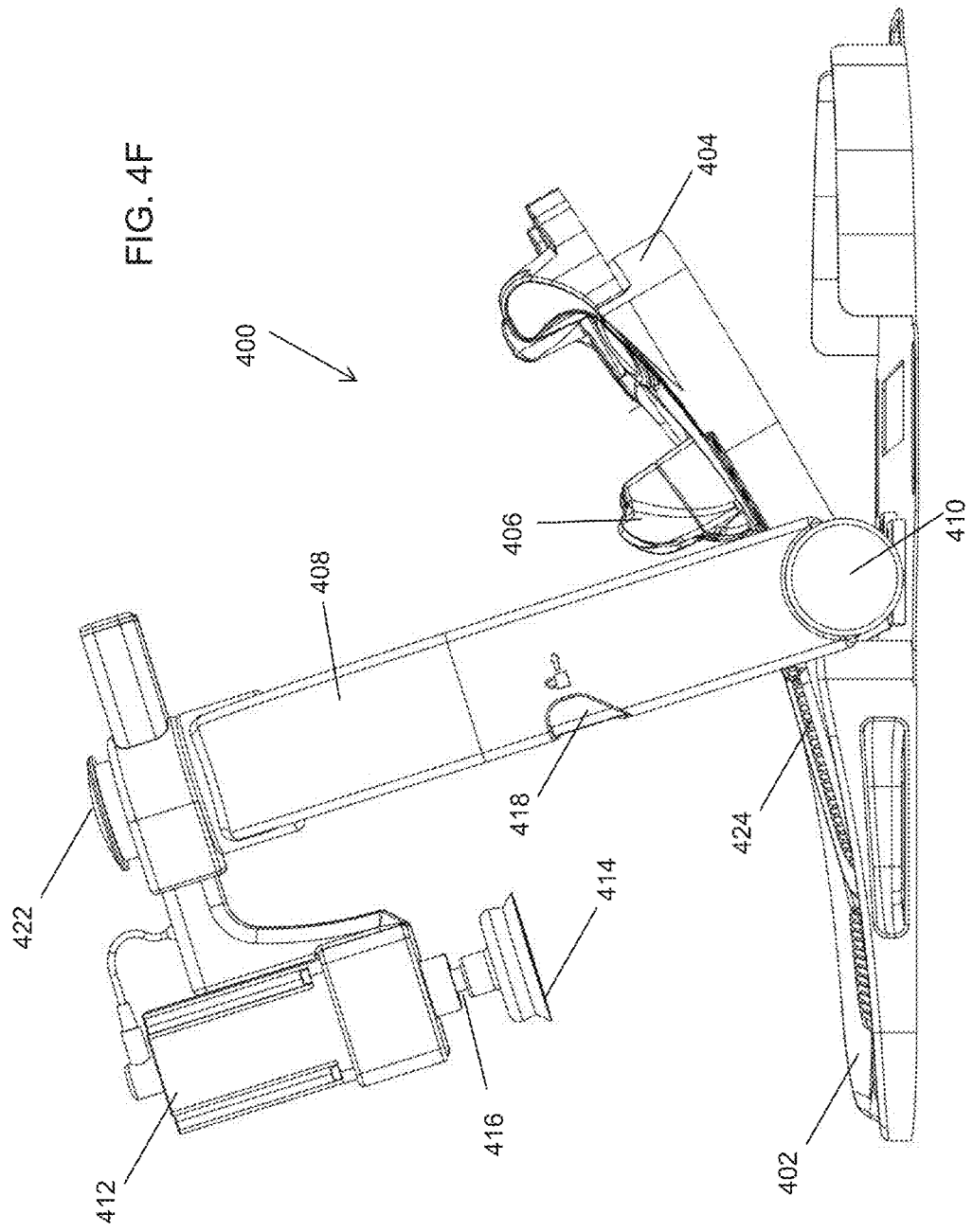

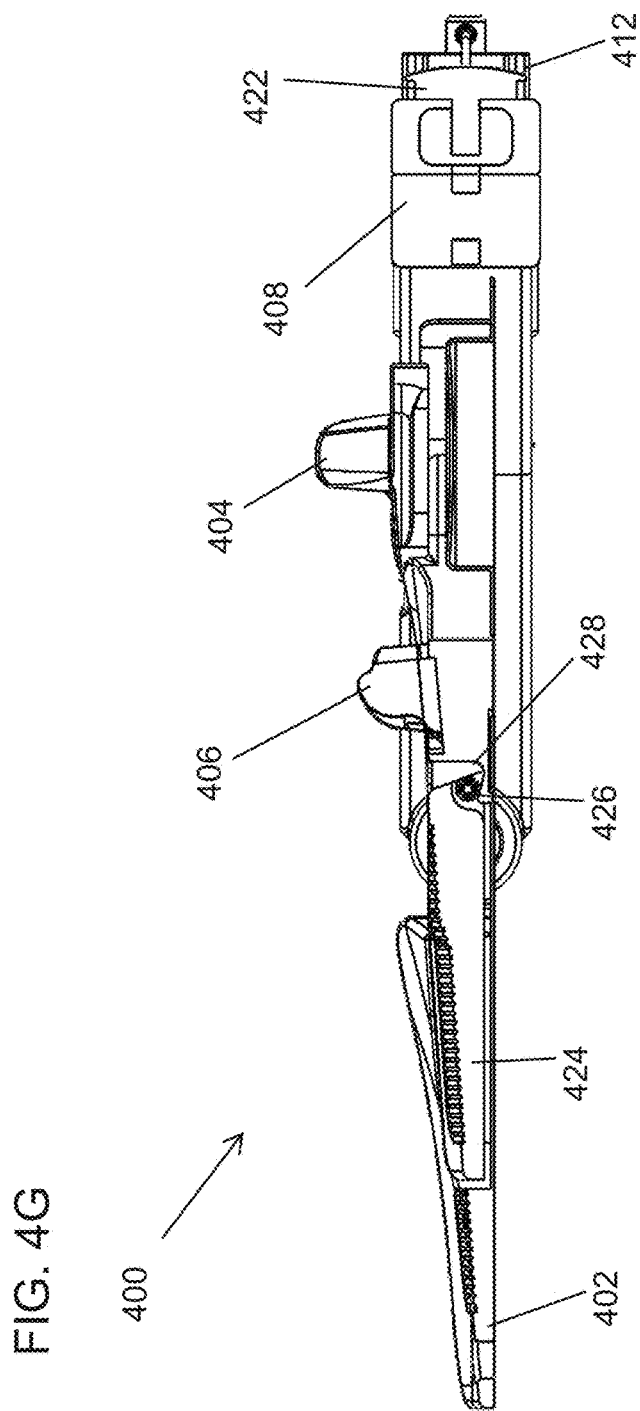

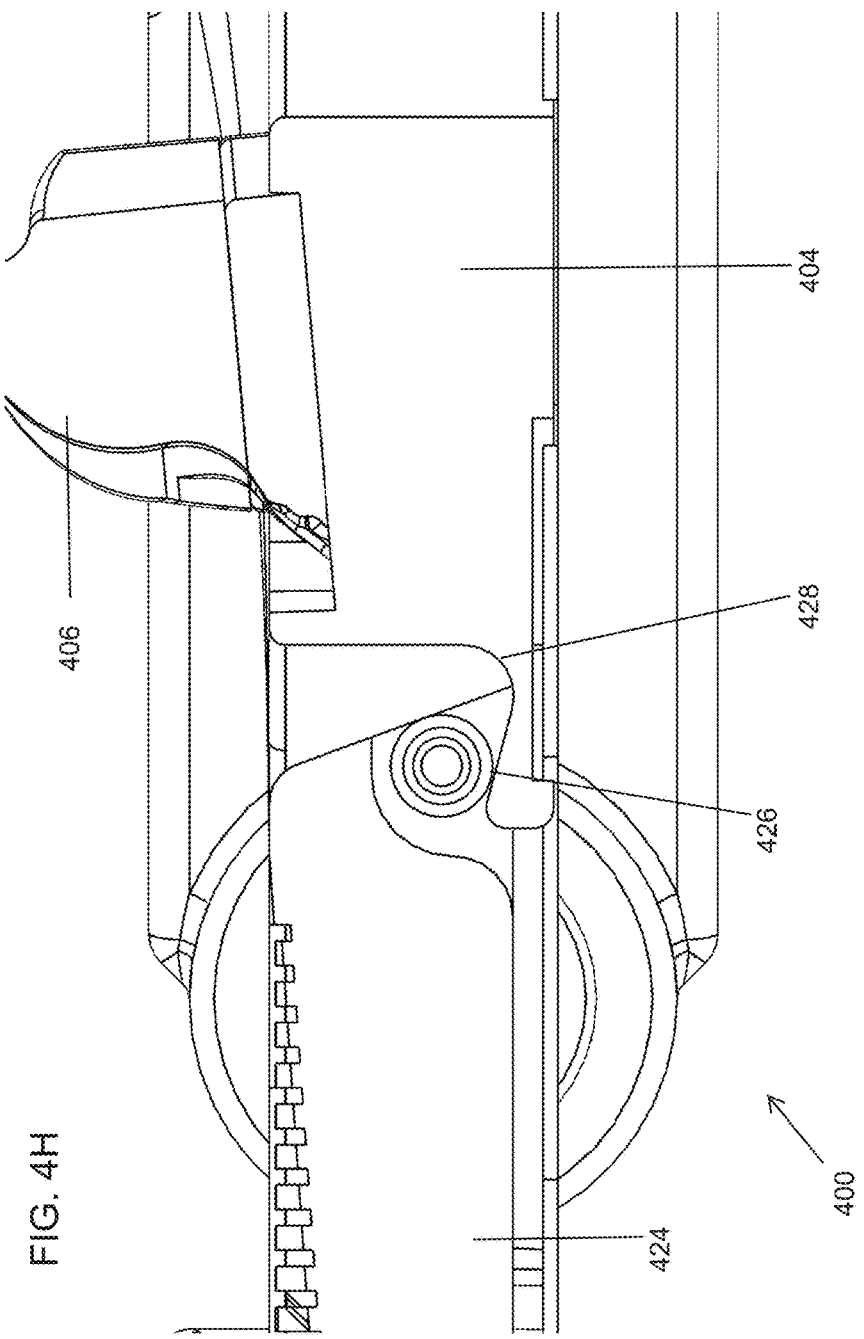

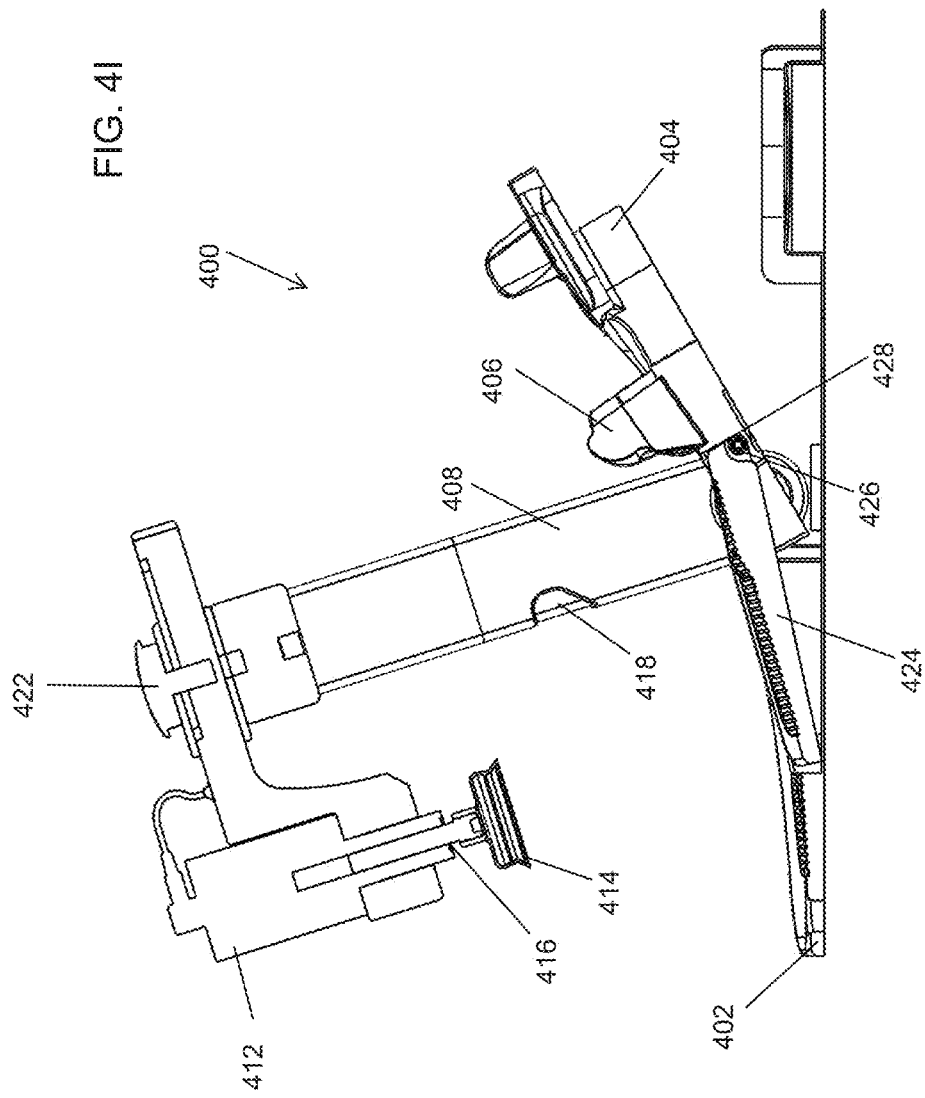

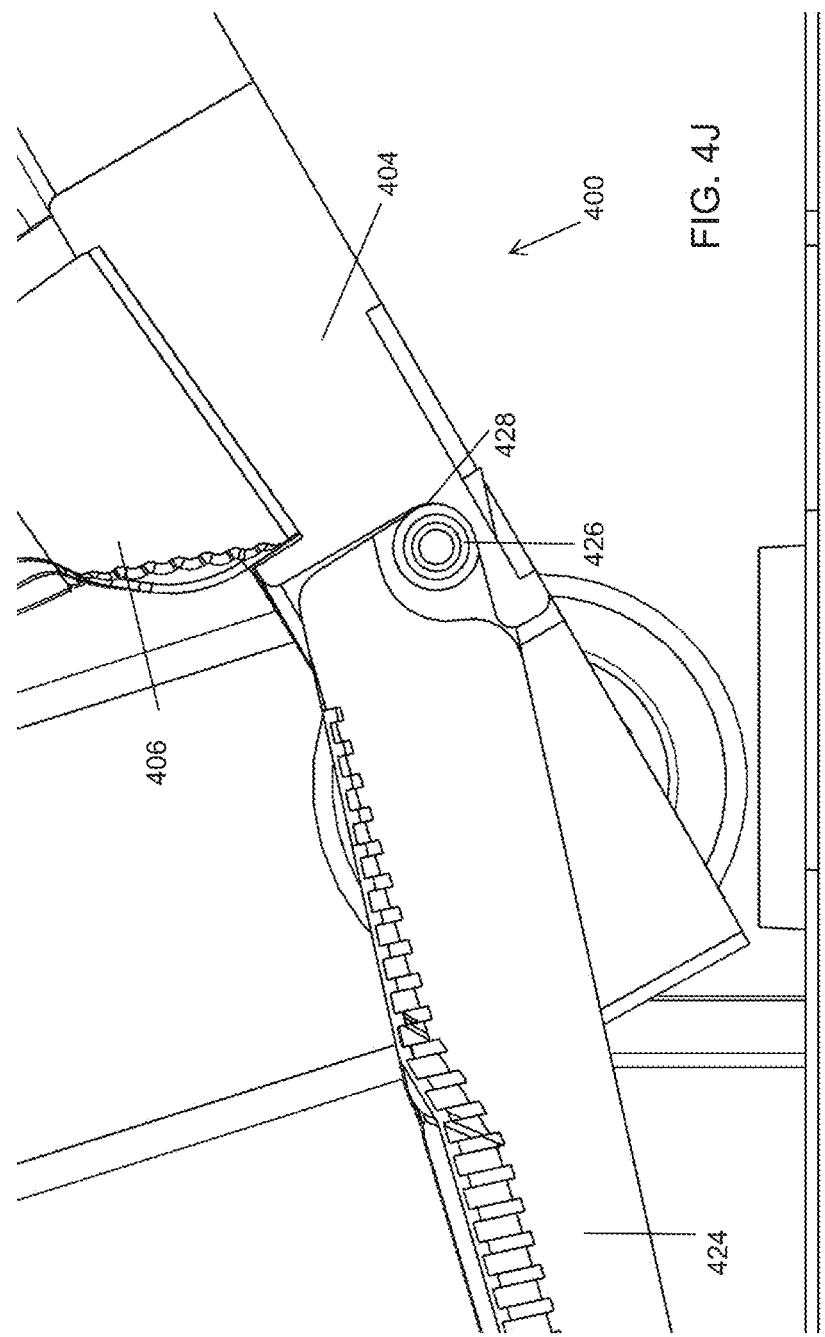

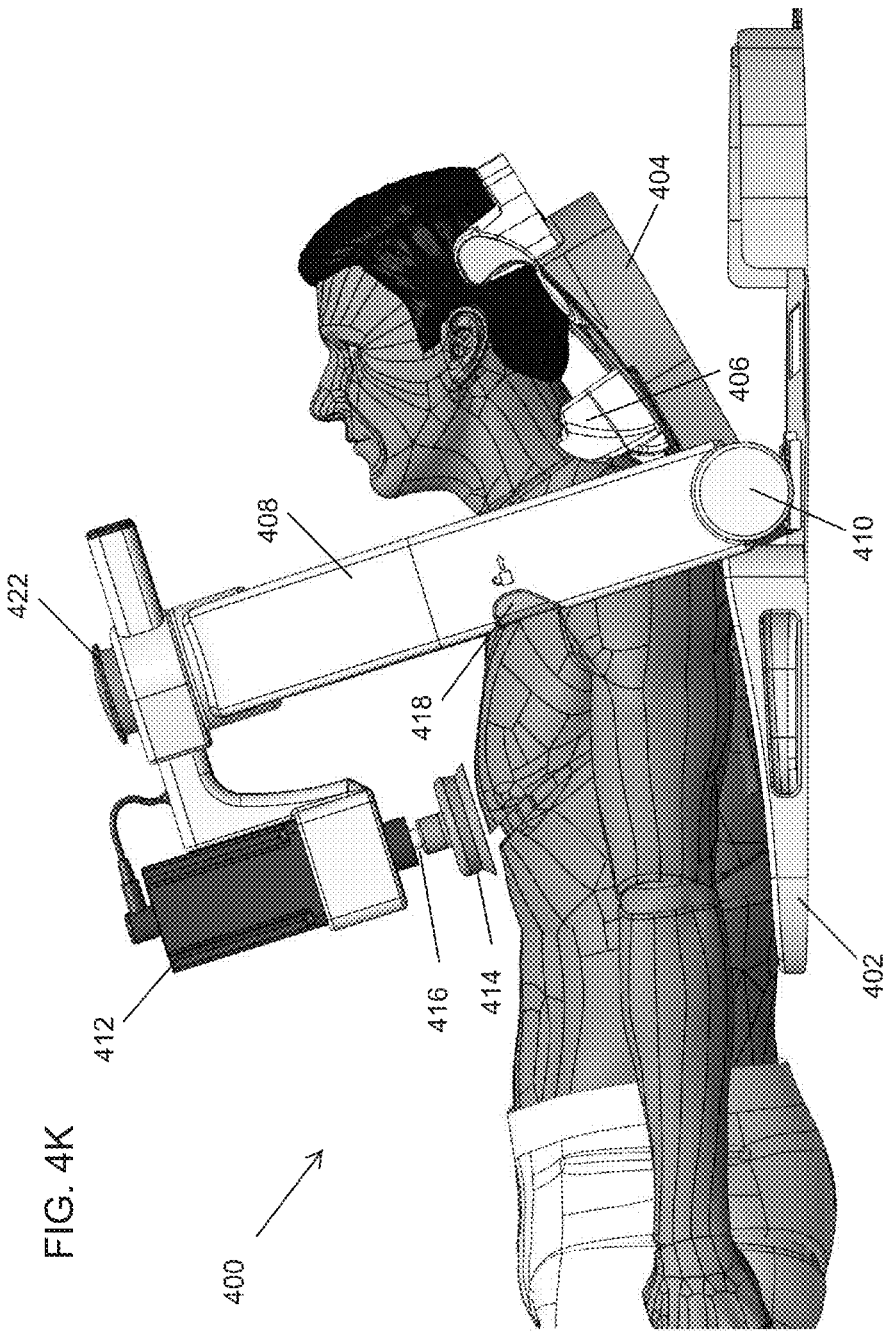

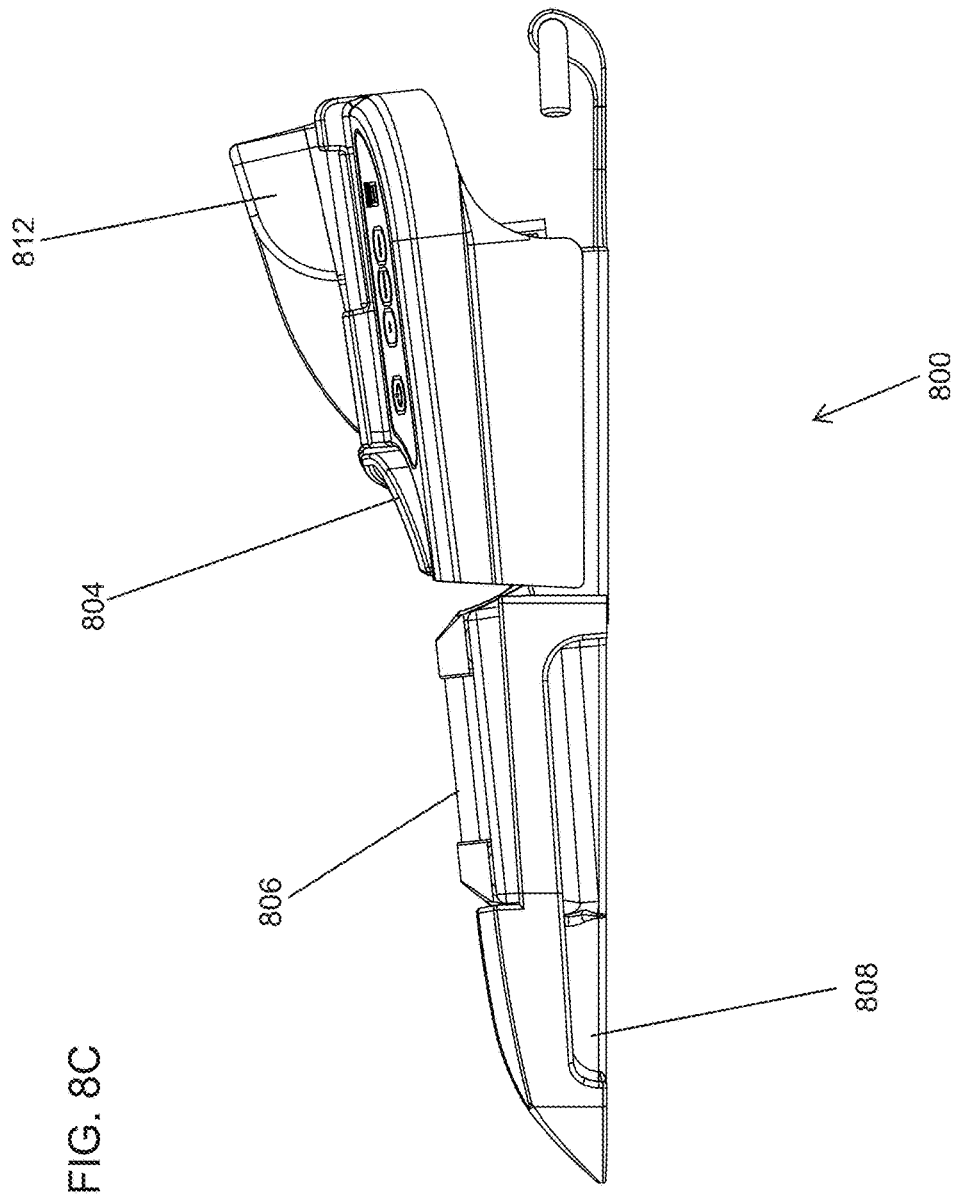

ELEVATION TIMING SYSTEMS AND METHODS FOR HEAD UP CPR

CROSS-REFERENCES TO RELATED APPLICATIONS

This application is a continuation in part of U.S. application Ser. No. 15/285,063, filed Oct. 4, 2016, which is a continuation in part of U.S. application Ser. No. 15/160,492, filed May 20, 2016, which is a continuation in part of U.S. application Ser. No. 15/133,967, filed Apr. 20, 2016, which is a continuation in part of U.S. application Ser. No. 14/996,147, filed Jan. 14, 2016, which is a continuation in part of U.S. application Ser. No. 14/935,262, filed Nov. 6, 2015, which is a continuation in part of U.S. application Ser. No. 14/677,562, filed Apr. 2, 2015, which is a continuation of U.S. patent application Ser. No. 14/626,770, filed Feb. 19, 2015, which claims the benefit of U.S. Provisional Application No. 61/941,670, filed Feb. 19, 2014, U.S. Provisional Application No. 62/000,836, filed May 20, 2014, and U.S. Provisional Application No. 62/087,717, filed Dec. 4, 2014, the complete disclosures of which are hereby incorporated by reference for all intents and purposes.

U.S. application Ser. No. 14/935,262, filed Nov. 6, 2015 (referenced above) also claims the benefit of U.S. Provisional Application No. 62/242,655, filed Oct. 16, 2015, the complete disclosure of which is hereby incorporated by reference for all intents and purposes.

BACKGROUND OF THE INVENTION

The vast majority of patients treated with conventional (C) cardiopulmonary resuscitation (CPR) never wake up after cardiac arrest. Traditional closed-chest CPR involves repetitively compressing the chest in the med-sternal region with a patient supine and in the horizontal plane in an effort to propel blood out of the non-beating heart to the brain and other vital organs. This method is not very efficient, in part because refilling of the heart is dependent upon the generation of an intrathoracic vacuum during the decompression phase that draws blood back to the heart. Conventional (C) closed chest manual CPR (C-CPR) typically provides only 8-30% of normal blood flow to the brain and heart. In addition, with each chest compression, the arterial pressure increases immediately. Similarly, with each chest compression, right-side heart and venous pressures rise to levels nearly identical to those observed on the arterial side. The high right-sided pressures are in turn transmitted to the brain via the paravertebral venous plexus and jugular veins. The simultaneous rise of arterial and venous pressure with each C-CPR compression generates contemporaneous bi-directional (venous and arterial) high pressure compression waves that bombard the brain within the closed-space of the skull. This increase in blood volume and pressure in the brain with each chest compression in the setting of impaired cerebral perfusion further increases intracranial pressure (ICP), thereby reducing cerebral perfusion. These mechanisms have the potential to further reduce brain perfusion and cause additional damage to the already ischemic brain tissue during C-CPR.

To address these limitations, newer methods of CPR have been developed that significantly augment cerebral and cardiac perfusion, lower intracranial pressure during the decompression phase of CPR, and improve short and long-term outcomes. These methods may include the use of a load-distributing band, active compression decompression (ACD)+CPR, an impedance threshold device (ITD), active intrathoracic pressure regulation devices, and/or combinations thereof. However, despite these advances, most patients still do not wake up after out-of-hospital cardiac arrest. In the current invention the clinical benefits of each of these CPR methods and devices are improved when performed in the head and thorax up position.

BRIEF SUMMARY OF THE INVENTION

Embodiments of the invention are directed toward systems, devices, and methods of administering CPR to a patient in a head and thorax up position. Such techniques result in lower right-atrial pressures and intracranial pressure while increasing cerebral perfusion pressure, cerebral output, and systolic blood pressure (SBP) compared with CPR administered to an individual in the supine position. The configuration may also preserve a central blood volume and lower pulmonary vascular resistance and circulate drugs used during CPR more effectively. This provides a more effective and safe method of performing CPR for extended periods of time. The head and thorax up configuration may also preserve the patient in the sniffing position to optimize airway management and reduce complications associated with endotracheal intubation.

In one aspect, a method for performing CPR is provided. The method may include elevating the head, heart and shoulders of an individual from a starting elevation angle to a final elevation angle greater than zero degrees relative to horizontal while performing CPR by repeatedly compressing the chest. The method may also include regulating the intrathoracic pressure of the individual while performing CPR and, after stopping the performance of chest compressions, promptly lowering the head, heart, and shoulders from the final elevation angle within a clinically-desirable timeframe selected to prevent significant reduction in brain blood flow until the head, heart and shoulders are lowered.

In another aspect, a method for performing CPR includes elevating the head, heart and shoulders of an individual from a starting elevation angle to a final elevation angle greater than zero degrees relative to horizontal to actively drain venous blood from the brain using gravity while performing CPR by repeatedly compressing the chest. Elevation of the head, heart and shoulders assists to lower intracranial pressure and increase cerebral perfusion pressure during the performance of CPR. The head, heart and shoulders may be elevated from the starting elevation angle to the final elevation angle within a clinically-desirable timeframe selected to enable enough blood flow to the brain even though the brain is being elevated. The method may also include regulating the intrathoracic pressure of the individual while performing CPR to create a negative pressure within the chest during a relaxation phase of CPR.

In another aspect, a system for performing CPR is provided. The system may include an elevation device having a base and an upper support operably coupled to the base. The upper support may be configured to elevate an individual's heart, shoulders and head from a starting elevation angle to a final elevation angle within a clinically-desirable time period selected to be slow enough to permit a sufficient amount of blood to flow to the brain during the elevation of the head, heart and shoulders.

In another aspect, a method for doubling blood flow to the brain after prolonged CPR is provided. The method may include performing chest compressions on an individual for a period of at least 15 minutes using an active compression decompression CPR device or a load-distributing band CPR device while the head, shoulders, and heart are elevated. The method may also include actively regulating an intrathoracic pressure of the individual during the performance of CPR, thereby doubling blood flow to the brain.

BRIEF DESCRIPTION OF THE DRAWINGS

A further understanding of the nature and advantages of various embodiments may be realized by reference to the following figures. In the appended figures, similar components or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

FIG. 4A depicts an isometric view of an elevation device in a stowed position according to embodiments.

FIG. 4B depicts a side view of the elevation device of FIG. 4A with a chest compression device in a stowed position according to embodiments.

FIG. 4C depicts a rear view of the elevation device of FIG. 4A with a chest compression device in a stowed position according to embodiments.

FIG. 4F depicts a side view of the elevation device of FIG. 4A with a chest compression device in an active position according to embodiments.

FIG. 4G depicts a mechanism for tilting a thoracic plate of the elevation device of FIG. 4A in a lowered position according to embodiments.

FIG. 4H depicts a mechanism for tilting a thoracic plate of the elevation device of FIG. 4A in a lowered position according to embodiments.

FIG. 4I depicts a mechanism for tilting a thoracic plate of the elevation device of FIG. 4A in an elevated position according to embodiments.

FIG. 4J depicts a mechanism for tilting a thoracic plate of the elevation device of FIG. 4A in an elevated position according to embodiments.

FIG. 4K depicts an individual positioned on the elevation device of FIG. 4A according to embodiments.

FIG. 8C depicts a side view of the elevation device of FIG. 8A with a raised head support according to embodiments.

DETAILED DESCRIPTION OF THE INVENTION

Figure 1A:
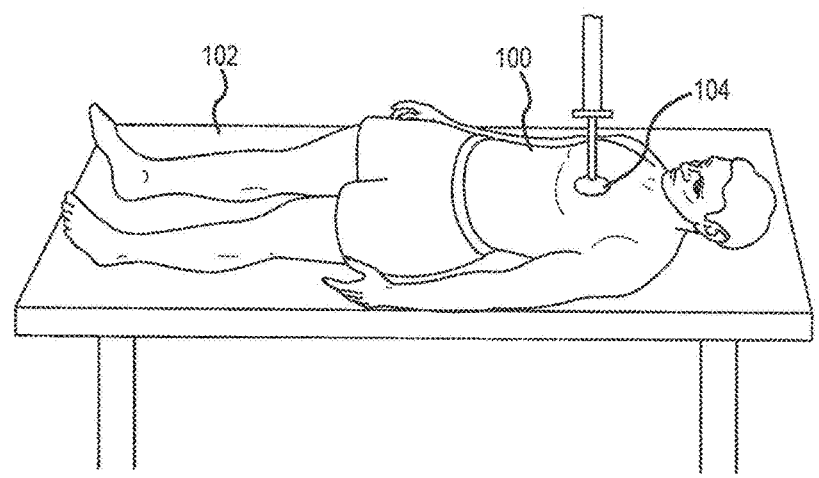
FIG. 1A is a schematic of a patient receiving CPR in a supine configuration according to embodiments.

One aspect of the invention involves CPR techniques where the entire body, and in some cases at least the head, shoulders, and heart, of a patient is tilted upward. This improves cerebral perfusion and cerebral perfusion pressures after cardiac arrest. In some cases, CPR with the head and heart elevated may be performed using any one of a variety of manual or automated conventional CPR devices (e.g. active compression-decompression CPR, load-distributing band, or the like) alone or in combination with any one of a variety of systems for regulating intrathoracic pressure, such as a threshold valve that interfaces with a patient's airway (e.g., an ITD), the combination of an ITD and a Positive End Expiratory Pressure valve (see Voelckel et al "The effects of positive end-expiratory pressure during active compression decompression cardiopulmonary resuscitation with the inspiratory threshold valve." *Anesthesia and Analgesia.* 2001 April: 92(4): 967-74, the entire contents of which is hereby incorporated by reference) or a Bousignac tube alone or coupled with an ITD (see U.S. Pat. No. 5,538,002, the entire contents of which is hereby incorporated by reference). In some cases, the systems for regulating intrathoracic pressure may be used without any type of chest compression. When CPR is performed with the head and heart elevated, gravity drains venous blood from the brain to the heart, resulting in refilling of the heart after each compression and a substantial decrease in ICP, thereby reducing resistance to forward brain flow. This maneuver also reduces the likelihood of simultaneous high pressure waveform simultaneously compressing the brain during the compression phase. While this may represent a potential significant advance, tilting the entire body upward, or at least the head, shoulders, and heart, has the potential to reduce coronary and cerebral perfusion during a prolonged resuscitation effort since over time gravity will cause the redistribution of blood to the abdomen and lower extremities.

It is known that the average duration of CPR is over 20 minutes for many patients with out-of-hospital cardiac arrest. To prolong the elevation of the cerebral and coronary perfusion pressures sufficiently for longer resuscitation efforts, in some cases, the head may be elevated at between about 10 cm and 30 cm (typically about 20 cm) while the thorax, specifically the heart and/or lungs, is elevated at between about 3 cm and 8 cm (typically about 10 cm) relative to a supporting surface and/or the lower body of the individual. Typically, this involves providing a thorax support and a head support that are configured to elevate the respective portions of the body at different angles and/or heights to achieve the desired elevation with the head raised higher than the thorax and the thorax raised higher than the lower body of the individual being treated. Such a configuration may result in lower right-atrial pressures while increasing cerebral perfusion pressure, cerebral output, and systolic blood pressure SBP compared to CPR administered to an individual in the supine position. The configuration may also preserve a central blood volume and lower pulmonary vascular resistance.

The head up devices (HUD) described herein mechanically elevate the thorax and the head, maintain the head and thorax in the correct position for CPR when head up and supine using an expandable and retractable thoracic back plate and a neck support, and allow a thoracic plate to angulate during head elevation so the piston of a CPR assist device always compresses the sternum in the same place and a desired angle (such as, for example, a right angle) is maintained between the piston and the sternum during each chest compression. Embodiments were developed to provide each of these functions simultaneously, thereby enabling maintenance of the compression point at the anatomically correct place when the patient is flat (supine) or their head and chest are elevated.

In some embodiments, it may be advantageous to carefully control the speed at which a patient is elevated and/or lowered before, during, and/or after CPR. For example, it is advantageous to elevate the head slowly when first starting CPR since the blood flow "uphill" is often barely adequate to provide sufficient blood flow to the head and brain. In other words, it takes time to pump blood uphill with the types of chest compression techniques described herein, so it is advantageous to elevate the patient's upper body slowly to make this uphill pumping easier. In contrast, blood drains rapidly from the head when the patient has no blood pressure and the head and upper body are elevated. As a result, there is a need to lower the head fairly rapidly to prevent blood loss in the brain if CPR is stopped while the head is elevated. Typically, this means that the patient's head and upper body may be elevated at a different rate than it is lowered. For example, the patient's head may be elevated over a period of between about 2 and 30 seconds, and typically between about 5 and 20 seconds. The patient's head may be lowered between about 1 and 10 seconds, and typically between about 1-5 seconds.

The elevation devices described herein may include and/or be used in conjunction with one or more physiological sensors to determine rates and timing of elevation and lowering. For example, the patient on the elevation device may be monitored using an electrocardiogram (ECG). The ECG may detect a regular heart rhythm even if the individual has no palpable pulse.

Based on this detection of the regular heart rhythm, it may be determined to stop the performance of chest compressions and to promptly lower the head, heart and shoulders to the horizontal plane. This ensures that when CPR is stopped and it is observed that there is a regular heart rhythm but there is an absence of a palpable pulse (a condition termed pulseless electrical activity), the head, heart, and shoulders are rapidly lowered so that excessive blood does not drain from the brain while attempting to lower the patient. In other words, although the patient may now have a stable or regular heart rhythm so that CPR could potentially be stopped, the patient's heart is not strong enough to keep pumping blood "uphill" and so the patient is quickly lowered so that the blood in the brain does not immediately drain. It will be appreciated that other sensors [e.g. blood pressure, end tidal $CO_2$, cerebral oximetry and flow, etc.] may be used in conjunction with the elevation device to determine: when to start and/or stop CPR, when to elevate and/or lower a patient's upper body, a degree of elevation of the patient's upper body, a rate of elevation or lowering of the patient's upper body, and/or other parameters of CPR and/or ITPR.

In some embodiments, the elevation and/or de-elevation speeds of an elevation device, such as elevation devices described in FIGS. 3-7C, may be regulated by a controller. For example, the controller may adjust an actuation speed of a motor or other elevation mechanism to raise or lower an upper support surface of the elevation device within the necessary time frame. In some embodiments, a hydraulic lift mechanism may be used to elevate the upper support surface. In such embodiments, the hydraulic lift mechanism may be gradually pressurized to elevate the upper support surface. To quickly lower the upper support surface, a pressure valve may be opened allowing the pressure within the hydraulic lift mechanism to quickly drop, allowing the upper support to be lowered to a generally supine position very rapidly. Other lock and release handle mechanical devices could also be used to slowly elevate and rapidly lower the head and upper thorax as medically needed.

Figure 1B:
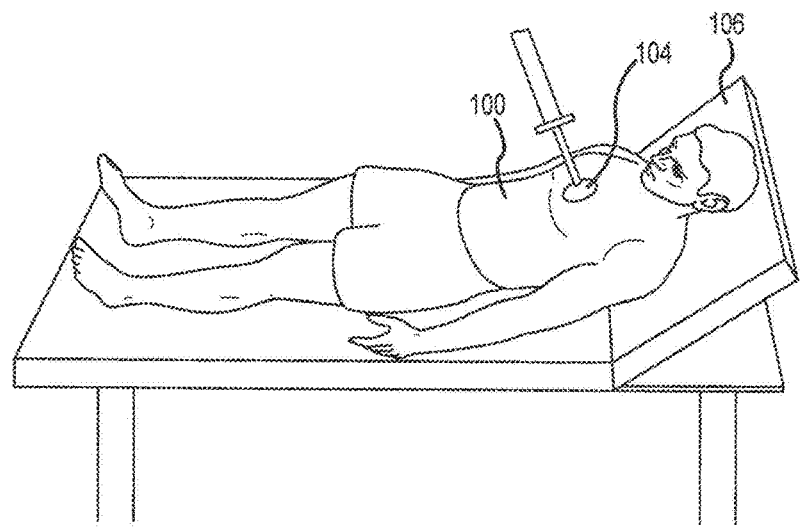
FIG. 1B is a schematic of a patient receiving CPR in a head and thorax up configuration according to embodiments.

Turning now to FIG. 1A, a demonstration of the standard supine (SUP) CPR technique is shown. Here, a patient 100 is positioned horizontally on a flat or substantially flat surface 102 while CPR is performed. CPR may be performed by hand and/or with the use of an automated CPR device and/or ACD+CPR device 104. In contrast, a head and thorax up (HUP) CPR technique is shown in FIG. 1B. Here, the patient 100 has his head and thorax elevated above the rest of his body, notably the lower body. The elevation may be provided by one or more wedges or angled surfaces 106 placed under the patient's head and/or thorax, which support the upper body of the patient 100 in a position where both the head and thorax are elevated, with the head being elevated above the thorax. HUP CPR may be performed with conventional standard CPR alone, with ACD alone, with the ITD alone, with the ITD in combination with conventional standard CPR alone, and/or with ACD+ITD together. Such methods regulate and better control intrathoracic pressure, causing a greater negative intrathoracic pressure during CPR when compared with conventional manual CPR. In some embodiments, HUP CPR may also be performed in conjunction with extracorporeal membrane oxygenation (ECMO).

Figure 2A:
FIG. 2A is a schematic showing a configuration of head up CPR according to embodiments.
Figure 2B:
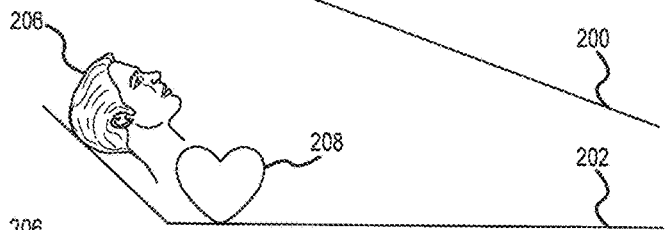
FIG. 2B is a schematic showing a configuration of head up CPR according to embodiments.
Figure 2C:
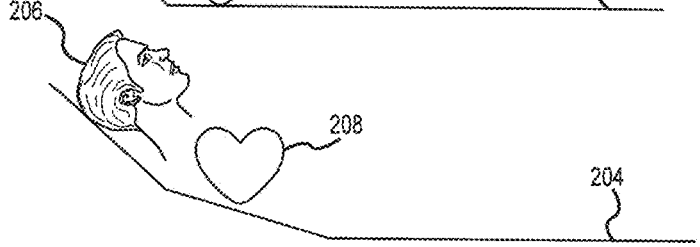
FIG. 2C is a schematic showing a configuration of head up CPR according to embodiments.

FIGS. 2A-2C demonstrate various set ups for HUP CPR as disclosed herein. Configuration 200 in FIG. 2A shows a user's entire body being elevated upward at a constant angle.

As noted above, such a configuration may result in a reduction of coronary and cerebral perfusion during a prolonged resuscitation effort since blood will tend to pool in the abdomen and lower extremities over time due to gravity. This reduces the amount of effective circulating blood volume and as a result blood flow to the heart and brain decrease over the duration of the CPR effort. Thus, configuration 200 is not ideal for administration of CPR over longer periods, such as those approaching average resuscitation effort durations. Configuration 202 in FIG. 2B shows only the patient's head 206 being elevated, with the heart and thorax 208 being substantially horizontal during CPR. Without an elevated thorax 208, however, systolic blood pressures and coronary perfusion pressures are lower as lungs are more congested with blood when the thorax is supine or flat. This, in turn, increases pulmonary vascular resistance and decreases the flow of blood from the right side of the heart to the left side of the heart when compared to CPR in configuration 204. Configuration 204 in FIG. 2C shows both the head 206 and heart/thorax 208 of the patient elevated, with the head 206 being elevated to a greater height than that heart/thorax 208. This results in lower right-atrial pressures while increasing cerebral perfusion pressure, cerebral output, and systolic blood pressure compared to CPR administered to an individual in the supine position, and may also preserve a central blood volume and lower pulmonary vascular resistance.

Figure 3:
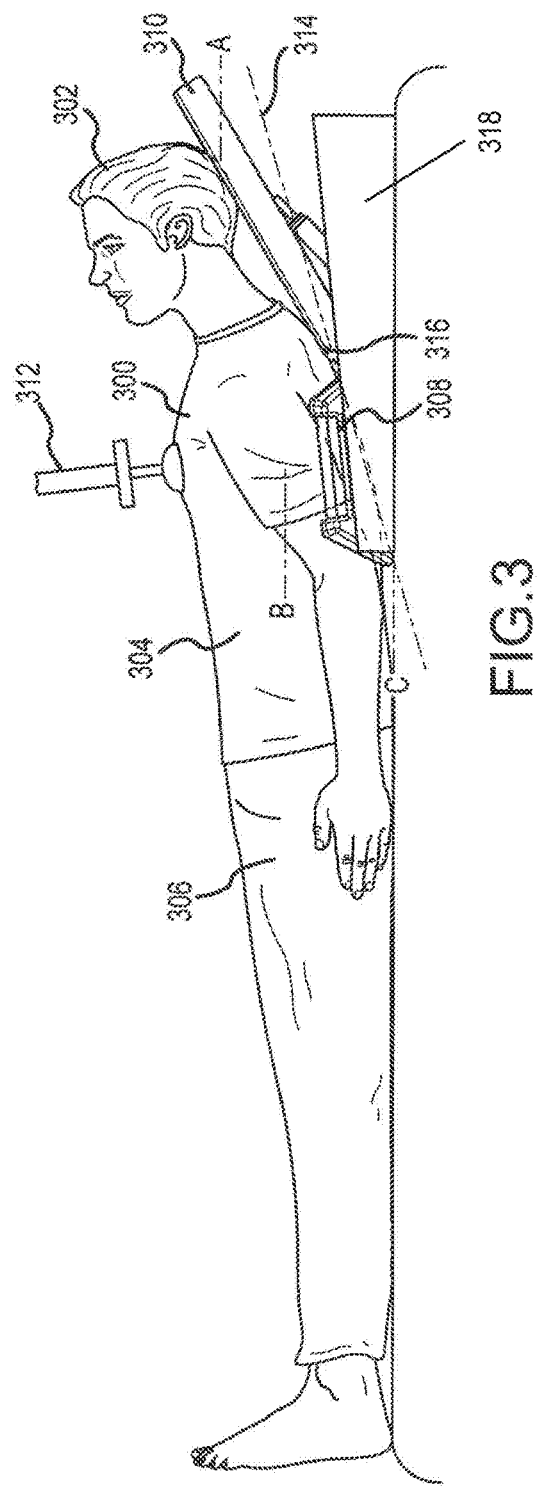
FIG. 3 shows a patient receiving CPR in a head and thorax up configuration according to embodiments.

FIG. 3 depicts a patient 300 having the head 302 and thorax 304 elevated above the lower body 306 using an elevation device 318. This may be done, for example, by using one or more supports of elevation device 318 to position the patient 300 appropriately. Here thoracic support 308 is positioned under the thorax 304 to elevate the thorax 304 to a desired height B, which is typically between about 3 cm and 8 cm. Upper support 310 is positioned under the head 302 such that the head 302 is elevated to a desired height A, typically between about 10 cm and 30 cm. Thus, the patient 300 has its head 302 at a higher height A than thorax at height B, and both are elevated relative to the flat or supine lower body at height C. Typically, the height of thoracic support 308 may be achieved by the thoracic support 308 being at an angle of between about 0° and 15° from a substantially horizontal plane with which the patient's lower body 306 is aligned. Upper support 310 is often at an angle between about 15° and 45° above the substantially horizontal plane. In some embodiments, one or both of the upper support 310 and thoracic support 308 is adjustable such that an angle and/or height may be altered to match a type a CPR, ITP regulation, and/or body size of the individual. As shown here, thoracic plate or support 308 is fixed at an angle, such as between 0° and 15° from a substantially horizontal plane. The upper support 310 may adjust by pivoting about an axis 314. This pivoting may involve a manual adjustment in which a user pulls up or pushes down on the upper support 310 to set a desired position. In other embodiments, the pivoting may be driven by a motor or other drive mechanism. For example, a hydraulic lift coupled with an extendable arm may be used. In other embodiments, a screw or worm gear may be utilized in conjunction with an extendable arm or other linkage. Any adjustment or pivot mechanism may be coupled between a base of the support structure and the upper support 310 In some embodiments, a neck support may be positioned on the upper support to help maintain the patient in a proper position.

In some embodiments, the elevation and/or de-elevation speeds of elevation device 318 may be regulated by a controller. For example, the controller may adjust an actuation speed of a motor or other elevation mechanism to raise or lower an upper support surface of the elevation device within the necessary time frame. In some embodiments, the controller may receive data from one or more physiological sensors and use this data to determine rates and timing of elevation and lowering. For example, the patient on the elevation device 318 may be monitored using an electrocardiogram (ECG). The ECG may detect a stable heart rhythm even if the individual has no palpable pulse. Based on this detection of the stable heart rhythm, it may be determined to promptly lower the head, heart and shoulders and to determine whether or not there is a palpable pulse without the performance of CPR. For example, once it is detected that the patient has a stable heart rhythm, the controller may alert medical personnel that chest compressions should be ceased, and may send a signal to the motor or other actuator to cause the upper support 310 to rapidly lower. In some embodiments, alerting medical personnel may involve producing a visual indicator, such as lighting up a light emitting diode (LED) or other light source and/or presenting a textual and/or image-based display on a screen of the elevation device 318. In one embodiment, upon detecting a stable heart rhythm, the controller may send a command to an automatic chest compression device (not shown) that causes the chest compression device to stop the delivery of chest compressions and/or decompressions. The rapid lowering immediately upon detection that the patient has a stable heart rhythm ensures that excessive blood does not drain from the brain while attempting to lower the patient. It will be appreciated that other sensors may be used in conjunction with the elevation device 318 to determine: when to start and/or stop CPR, when to elevate and/or lower a patient's upper body, a degree of elevation of the patient's upper body, a rate of elevation or lowering of the patient's upper body, and/or other parameters of CPR and/or ITPR.

As one example, the lower body 306 may define a substantially horizontal plane. A first angled plane may be defined by a line formed from the patient's chest 304 (heart and lungs) to his shoulder blades. A second angled plane may be defined by a line from the shoulder blades to the head 302. The first plane may be angled about between 5° and 15° above the substantially horizontal plane and the second plane may be at an angle of between about 15° and 45° above the substantially horizontal plane. In some embodiments, the first angled plane may be elevated such that the heart is at a height of about 4-8 cm above the horizontal plane and the head is at a height of about 10-30 cm above the horizontal plane.

The type of CPR being performed on the elevated patient may vary. Examples of CPR techniques that may be used include manual chest compression, chest compressions using an assist device such as chest compression device 312, either automated or manually, ACD CPR, a load-distributing band, standard CPR, stutter CPR, and the like. Such processes and techniques are described in U.S. Pat. Pub. No. 2011/0201979 and U.S. Pat. Nos. 5,454,779 and 5,645,522, all incorporated herein by reference. Further various sensors may be used in combination with one or more controllers to sense physiological parameters as well as the manner in which CPR is being performed. The controller may be used to vary the manner of CPR performance, adjust the angle of inclination, the speed of head and thorax rise and descent, provide feedback to the rescuer, and the like. Further, a compression device could be simultaneously applied to the lower extremities or abdomen to squeeze venous blood back into the upper body, thereby augmenting blood flow back to the heart. Further, a compression-decompression band could be applied to the abdomen that compresses the abdomen only when the head and thorax are elevated either continuously or in a pulsatile manner, in synchrony or asynchronously to the compression and decompression of the chest. Further, a rigid or semi-rigid cushion could be simultaneously inserted under the thorax at the level of the heart to elevate the heart and provide greater back support during each compression.

Additionally, a number of other procedures may be performed while CPR is being performed on the patient in the torso-elevated state. One such procedure is to periodically prevent or impede the flow in respiratory gases into the lungs. This may be done by using a threshold valve, sometimes also referred to as an impedance threshold device (ITD) that is configured to open once a certain negative intrathoracic pressure is reached. The invention may utilize any of the threshold valves or procedures using such valves that are described in U.S. Pat. Nos. 5,551,420; 5,692,498; 5,730,122; 6,029,667; 6,062,219; 6,810,257; 6,234,916; 6,224,562; 6,526,973; 6,604,523; 6,986,349; and 7,204,251, the complete disclosures of which are herein incorporated by reference.

Another such procedure is to manipulate the intrathoracic pressure in other ways, such as by using a ventilator or other device to actively withdraw gases from the lungs. Such techniques as well as equipment and devices for regulating respirator gases are described in U.S. Pat. Pub. No. 2010/0031961, incorporated herein by reference. Such techniques as well as equipment and devices are also described in U.S. patent application Ser. Nos. 11/034,996 and 10/796,875, and also U.S. Pat. Nos. 5,730,122; 6,029,667; 7,082,945; 7,410,649; 7,195,012; and 7,195,013, the complete disclosures of which are herein incorporated by reference.

In some embodiments, the angle and/or height of the head and/or heart may be dependent on a type of CPR performed and/or a type of intrathoracic pressure regulation performed. For example, when CPR is performed with a device or device combination capable of providing more circulation during CPR, the head may be elevated higher, for example 10-30 cm above the horizontal plane (10-45 degrees) such as with ACD+ITD CPR. When CPR is performed with less efficient means, such as manual conventional standard CPR, then the head may be elevated less, for example 10-20 cm or 10 to 20 degrees.

A variety of equipment or devices may be coupled to or associated with the structure used to elevate the head and torso to facilitate the performance of CPR and/or intrathoracic pressure regulation. For example, a coupling mechanism, connector, or the like may be used to removably couple a CPR assist device to the structure. This could be as simple as a snap fit connector to enable a CPR assist device to be positioned over the patient's chest. Examples of CPR assist devices that could be used with the elevation device (either in the current state or a modified state) include the Lucas device, sold by Physio-Control, Inc. and described in U.S. Pat. No. 7,569,021, the entire contents of which is hereby incorporated by reference, the Defibtech Lifeline ARM—Hands-Free CPR Device, sold by Defibtech, the Thumper mechanical CPR device, sold by Michigan Instruments, automated CPR devices by Zoll, such as the AutoPulse, as also described in U.S. Pat. No. 7,056,296, the entire contents of which is hereby incorporated by reference, the Weil Mini Chest Compressor Device, such as described in U.S. Pat. No. 7,060,041 (Weil Institute), and the like.

As an individual's head is elevated using an elevation device, such as elevation device 318, the individual's thorax is forced to constrict and compress, which causes a more magnified thorax migration during the elevation process. This thorax migration may cause the misalignment of a chest compression device, which leads to ineffective, and in some cases, harmful, chest compressions. It can also cause the head to bend forward thereby potentially restricting the airway. Thus, maintaining the individual in a proper position throughout elevation, without the compression and contraction of the thorax, is vital to ensure that safe and effective CPR can be performed. Embodiments of the elevation devices described herein provide upper supports that may expand and contract, such as by sliding along a support frame to permit the thorax to move freely upward and remain elongate, rather than contract, during the elevation process. For example, the upper support may be supported on rollers with minimal friction. As the head, neck, and/or shoulders are lifted, the upper support may slide away from the thoracic compression, which relieves a buildup of pressure on the thorax and minimizes thoracic compression and migration. Additionally, such elevation devices are designed to maintain optimal airway management of the individual, such as by supporting the individual in the sniffing position throughout elevation. In some embodiments, the upper supports may be spring biased in a contraction direction such that the only shifting or expansion of the upper support is due to forces from the individual as the individual is subject to thoracic shift. Other mechanisms may be incorporated to combat the effects of thoracic shift. For example, adjustable thoracic plates may be used that adjust angularly relative to the base to ensure that the chest compression device remains properly aligned with the individual's sternum. Typically, the thoracic plate may be adjusted between an angle of between about 0° and 8° from a substantially horizontal plane. In some embodiments, as described in greater detail below, the adjustment of the thoracic plate may be driven by the movement of the upper support. In such embodiments, a proper amount of thoracic plate adjustment can be applied based on the amount of elevation of the upper support.

In traditional CPR the patient is supine on an underlying flat surface while manual or automated CPR is implemented. During automated CPR, the chest compression device may migrate due to limited stabilization to the underlying flat surface, and may often require adjustment due to the migration of the device and/or body migration. This may be further exaggerated when the head and shoulders are raised. The elevation devices described herein offer a more substantial platform to support and cradle the chest compression device, such as, for example, a LUCAS device, providing stabilization assistance and preventing unwanted migratory motion, even when the upper torso is elevated. The elevation devices described herein provide the ability to immediately commence CPR in the lowered/supine position, continuing CPR during the gradual, controlled rise to the "Head-Up/Elevated" position. Such elevation devices provide ease of patient positioning and alignment for automated CPR devices. Correct positioning of the patient is important and readily accomplished with guides and alignment features, such as a shaped shoulder profile, a neck/shoulder support, a contoured thoracic plate, as well as other guidelines and graphics. The elevation devices may incorporate features that enable micro adjustments to the position of an automated CPR device position, providing control and enabling accurate placement of the automated CPR device during the lift process. In some embodiments, the elevation devices may establish the sniffing position for intubation when required, in both the supine position and during the lifting process. Features such as stationary pads and adjustable cradles may allow the reduction of neck extension as required while allowing ready access to the head for manipulation during intubation.

Figure 4D:
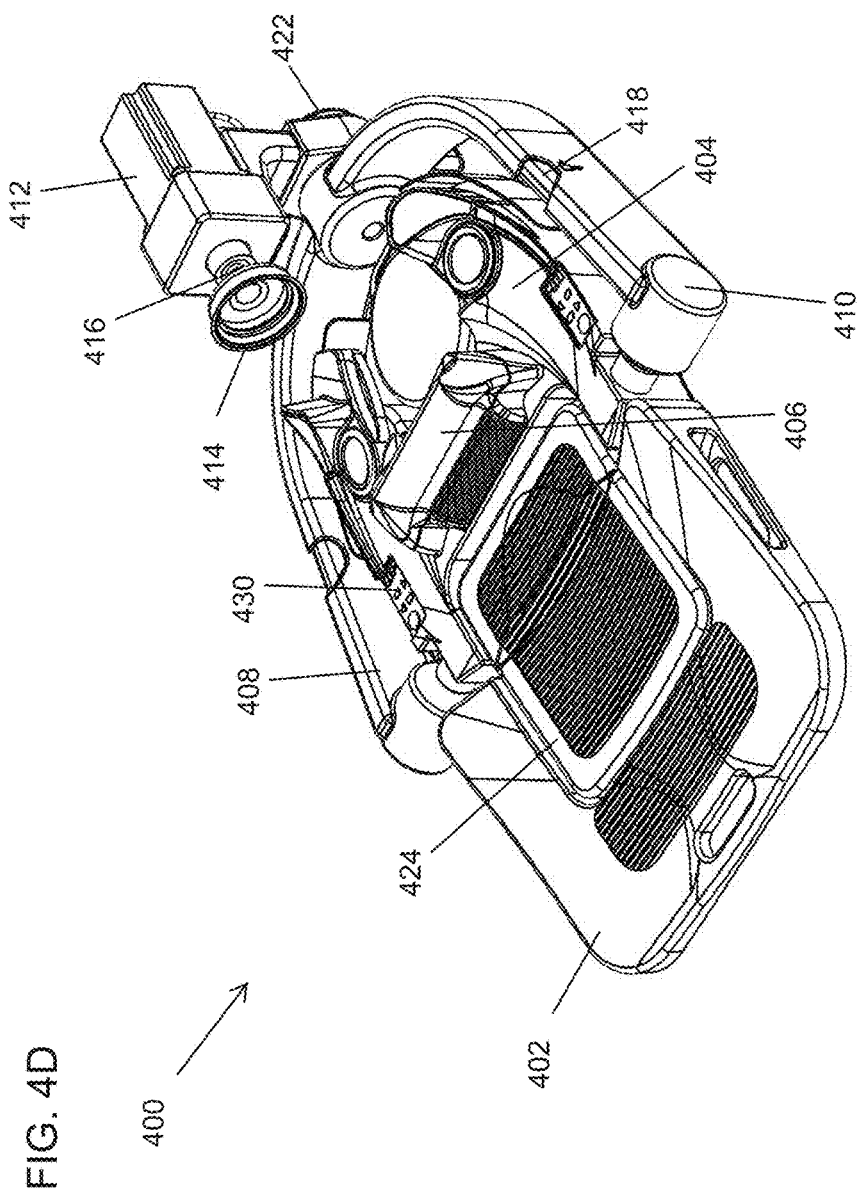
FIG. 4D depicts an isometric view of the elevation device of FIG. 4A with a chest compression device in an intermediate position according to embodiments.

FIGS. 4A-4K depict an example of an elevation device 400, which may be similar to other elevation devices described herein. This device is designed to be placed under the patient as soon as a cardiac arrest is diagnosed. It has a low profile designed to slip under the patient's body rapidly and easily. For example, FIG. 4A shows that elevation device 400 may include a base 402 that supports and is pivotally or otherwise operably coupled with an upper support 404. Upper support 404 may include a neck pad or neck support 406, as well as areas configured to receive a patient's upper back, shoulders, neck, and/or head. An elevation mechanism may be configured to adjust the height and/or angle of the upper support 404 throughout the entire ranges of 0° and 45° relative to the horizontal plane and between about 10 cm and 40 cm above the horizontal plane. Upper support 404 may be configured to be adjustable such that the upper support 404 may slide along a longitudinal axis of base 402 to accommodate patients of different sizes as well as movement of a patient associated with the elevation of the head by upper support 404. In some embodiments, this sliding movement may be locked once an individual is positioned on the elevated upper support 404. In some embodiments, the upper support 404 may include one or more springs that may bias the upper support 404 toward the torso. This allows the upper support 404 to slide in a controlled manner when the individual's body shifts during the elevation process. In some embodiments, the one or more springs may have a total spring force of between about 10 lb. and about 50 lbs., more commonly between about 25 lb. and about 30 lb. Such force allows the upper support 404 to maintain a proper position, yet can provide some give as the head and upper torso are elevated. Further, the elevation device may include a slide mechanism such that with elevation of the head and neck the portion of elevation device behind the head and shoulder elongates. This helps to maintain the neck in the sniffing position.

Elevation device 400 may also include a support arm 408 that may rotate about a pivot point 410 or other rotational axis. In some embodiments, rotational axis 410 may be coaxially aligned with a rotational axis of the upper support 404. Support arm 408 that may rotate between and be locked into a stowed position in which the support arm 408 is at least substantially in plane with the elevation device 400 when the upper support 404 is lowered as shown in FIG. 4B and an active position in which the support arm 408 is positioned substantially orthogonal to a patient's chest. The support arm 408 is shown in the active position in FIG. 4E. Turning back to FIG. 4B, the support arm 408 may be coupled with a chest compression device 412, which may be secured to the patient's chest using an adhesive material and/or suction cup 414 positioned on a lower portion of a plunger 416. In some embodiments, the support arm 408 may be configured to tilt along with the patient's chest as the head, neck, and shoulders are elevated by the upper support 404. The support arm 408 is movable to various positions relative to the upper support 404 and is lockable at a fixed angle relative to the upper support 404 such that the upper support 404 and the support arm 408 are movable as a single unit relative to the base 402 while the support arm 408 maintains the angle relative to the upper support 404 while the upper support 404 is being elevated. For example, the support arm 408 and upper support 404 may be rotated at a same rate about rotational axis 410. In some embodiments, the support arm 408 may be moved independently from the upper support 404. For example, when in the stowed position, a lock mechanism 44 of the support arm 408 may be disengaged, allowing the support arm 408 to being freely rotated. This allows the support arm 408 to be moved to the active position. Once in the active position, lock mechanism 44 may be engaged to lock the movement of the support arm 408 with the upper support 404.

In some embodiments, a position of the chest compression device 412 may be adjusted relative to the support arm 408. For example, the chest compression device 412 may include a slot or track 420 that may be engaged with a fastener, such as a set screw 422 on the support arm 408 as shown in FIG. 4C. The set screw 422 or other fastener may be loosened, allowing the chest compression device 412 to be repositioned to accommodate individuals of various sizes. Once properly adjusted, the set screw 422 may be inserted within the track 420 and tightened to secure the chest compression device 412 in the desired position.

FIG. 4D shows the chest compression device 412 of elevation device 400 in an intermediate position, with the chest compression device 412 being rotated out of alignment with the support arm 408. Here, the chest compression device 412 is generally orthogonal to the support arm 408. This is often done prior to maneuvering the support arm 408 to the active position, although in some cases, the support arm 408 may be moved prior to the chest compression device 412 to be rotated to the generally orthogonal position.

Figure 4E:
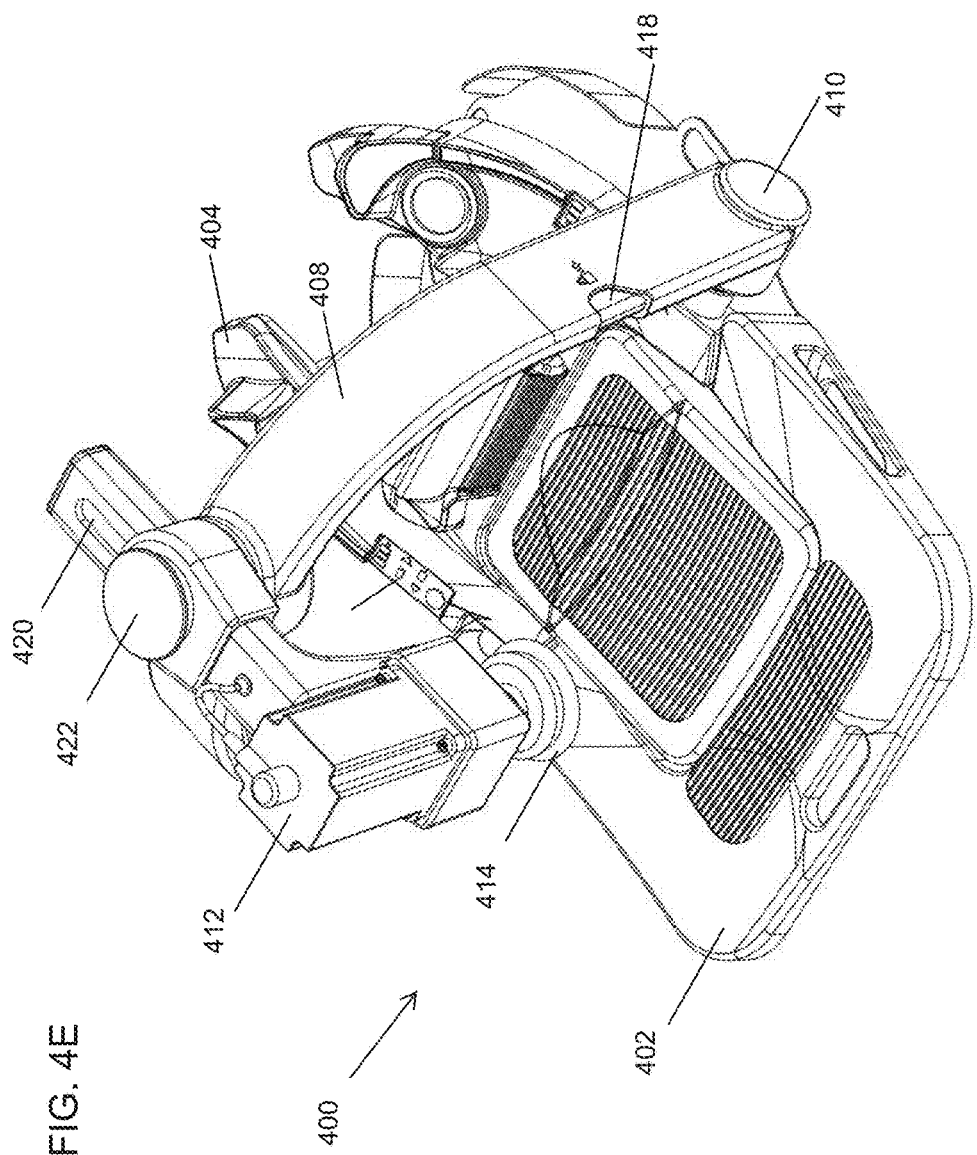
FIG. 4E depicts an isometric view of the elevation device of FIG. 4A with a chest compression device in an active position according to embodiments.

FIG. 4E shows upper support 404 of the elevation device 400 in an elevated position and support arm 408 in an active position. Here, support arm 408 is positioned such that the chest compression device 412 is aligned generally orthogonal to the individual's sternum. In some embodiments, the elevation of the upper support 404 and/or the support arm 408 may be actuated using a motor (not shown). Oftentimes, a control interface 430 may be included on the elevation device 400, such as on base 402. The control interface 430 may include one or more buttons or other controls that allow a user to elevate and/or lower the upper support 404 and/or support arm 408. In other embodiments, the motor may be controlled remotely using Bluetooth communication or other wired and/or wireless techniques. In some embodiments, the compression/decompression movement of the chest compression device 412 and/or elevation/lowering of the upper support 404 may be automatically regulated by a controller. Operation of the controller may be based upon physiological feedback from one or more sensors directly or indirectly attached to the patient.

In one embodiment, a controller may adjust an actuation speed of a motor or other elevation mechanism to raise or lower an upper support surface of the elevation device within the necessary time frame. For example, medical personnel may set a desired elevation time, such as between about 2 and 30 seconds. The controller will then operate a motor or other elevation mechanism to slowly raise the upper support 404 from a starting elevation angle to a final elevation angle over the selected time period. The controller may also instruct the elevation mechanism to quickly lower the upper support 404 within a desired timeframe, often between about 1 and 10 seconds. In some embodiments, the controller may receive data from one or more physiological sensors and use this data to determine rates and timing of elevation and lowering. For example, the patient on the elevation device 400 may be monitored using an electrocardiogram (ECG). The ECG may detect a stable heart rhythm even if the individual has no palpable pulse. Based on this detection of the stable heart rhythm, it may be determined to stop the performance of chest compressions and to promptly lower the upper support 404. For example, once it is detected that the patient has a stable heart rhythm, the controller may alert medical personnel that chest compressions should be ceased, and may send a signal to the motor or other actuator to cause the upper support 404 to rapidly lower. In some embodiments, alerting medical personnel may involve producing a visual indicator, such as lighting up a light emitting diode (LED) or other light source and/or presenting a textual and/or image-based display on a screen of the elevation device 400. In one embodiment, upon detecting a stable heart rhythm, the controller may send a command to the automatic chest compression device 412 that causes the chest compression device 412 to stop the delivery of chest compressions and/or decompressions. In another embodiment, upon detecting the stable heart rhythm, the controller will alert medical personnel, who may then operate the elevation device 400 to lower the upper support 404. It will be appreciated that other sensors may be used in conjunction with the elevation device 400 to determine: when to start and/or stop CPR, when to elevate and/or lower a patient's upper body, a degree of elevation of the patient's upper body, a rate of elevation or lowering of the patient's upper body, and/or other parameters of CPR and/or ITPR.

The chest compression device 412 may be similar to those described above. In some embodiments, to provide a stronger decompressive force to the chest, the chest compression device 412 may include one or more springs. For example, a spring (not shown) may be positioned around a portion of the plunger 416 above the suction cup 414. As the plunger 416 is extended downward by the motor (often with a linear actuator positioned there between), the spring may be stretched, thus storing energy. As the plunger 416 is retracted, the spring may recoil, providing sufficient force to actively decompress the patient's chest. In some embodiments, a spring (not shown) may be positioned near each pivot point 410 of support arm 408, biasing the rotatable arm in an upward, or decompression state. As the motor drives the plunger 416 and/or suction cup 414 to compress the patient's chest, the pivot point springs may also be compressed. As the tension is released by the motor, the pivot point springs may extend to their original state, driving the support arm 408 and suction cup 414 upward, thereby decompressing the patient's chest.

It will be appreciated that any number of tensioning mechanisms and drive mechanisms may be used to convert the force from the tensioning band or motor to an upward and/or downward linear force to compress the patient's chest. For example, a conventional piston mechanism may be utilized, such with tensioned bands and/or pulley systems providing rotational force to a crankshaft. In other embodiments, a pneumatically driven, hydraulically driver, and/or an electro-magnetically driven piston or plunger may be used. Additionally, the motor may be configured to deliver both compressions and decompressions, without the use of any springs. In other embodiments, both a spring around a plunger 416 and/or pivot point springs may be used in conjunction with a compression only or compression/decompression motor to achieve a desired decompressive force applied to the patient's chest. In still other embodiments, the motor and power supply, such as a battery, will be positioned in a portion of base 402 that is lateral or superior to the location of the patient's heart, such that they do not interfere with fluoroscopic, x-ray, or other imaging of the patient's heart during cardiac catheterization procedures. Further, the base 402 could include an electrode, attached to the portion of the device immediately behind the heart (not shown), which could be used as a cathode or anode to help monitor the patient's heart rhythm and be used to help defibrillate or pace the patient. As such, base 402 could be used as a 'work station' which would include additional devices such as monitors and defibrillators (not shown) used in the treatment of patients in cardiac arrest.

In some embodiments, the elevation device 400 includes an adjustable thoracic plate 424. The thoracic plate 424 may be configured to adjust angularly to help combat thoracic shift to help maintain the chest compression device 412 at a generally orthogonal to the sternum. The adjustment of the thoracic plate 424 may create a separate elevation plane for the heart, with the head being elevated at a greater angle using the upper support 404 as shown in FIG. 4F. In some embodiments, the thoracic plate 424 may be adjusted independently, while in other embodiments, adjustment of the thoracic plate 424 is tied to the elevation of the upper support 404. FIG. 4G shows a mechanism for adjusting the angle of the thoracic plate 424 in conjunction with elevation of the upper support 404. Here, elevation device 400 is shown with upper support 404 in a lowered position and support arm 408 in a stowed position. Thoracic plate 424 includes a roller 426 positioned on an elevation track 428 of upper support 404 as shown in FIG. 4II. The roller 426 may be positioned on a forward, raised portion of the elevation track 428. As the upper support 404 is elevated, the roller 426 is forced upward by elevation track 428, thereby forcing an end of the thoracic plate 424 proximate to the upper support 404 upwards as shown in FIGS. 4I and 4J. This causes the thoracic plate 424 to tilt, thus maintaining the chest at a generally orthogonal angle relative to the chest compression device 412. Oftentimes, elevation track 428 may be slanted from a raised portion proximate to the thoracic plate 424 to a lowered portion. The elevation track 428 may be tilted between about 4° and 20° to provide a measured amount of tilt relative to the thoracic shift expected based on a particular elevation level of the upper support 404. Typically, the thoracic plate 424 will be tilted at a lower angle than the upper support 404 is inclined.

FIG. 4K depicts elevation device 400 supporting an individual in an elevated and active position. Here, the user is positioned on the elevation device 400 with his neck positioned on the neck support 406. In some embodiments, the neck support 406 may contact the individual's spine at a location near the C7 and C8 vertebrae. This position may help maintain the individual in the sniffing position, to help enable optimum ventilation of the individual. In some embodiments, the individual may be aligned on the elevation device 400 by positioning his shoulders in alignment with the support arm 408. The chest compression device 412 is positioned in alignment with the individual's sternum at a generally orthogonal angle to ensure that the chest compressions are delivered at a proper angle and with proper force. In some embodiments, the alignment of the chest compression device 412 may be achieved may configuring the chest compression device 412 to pivot and/or otherwise adjust angularly to align the chest compression device 412 at an angle substantially orthogonal to the sternum. A linear position the chest compression device 412 may also be adjustable relative to the support arm 408 such that the plunger 416 and/or suction cup 414 of the chest compression device 412 may be moved up or down the individual's chest to ensure proper alignment of the plunger 416 and/or suction cup 414 with the sternum.

In some embodiments, the support arm 408 may be generally U-shaped and may be coupled with the base 402 on both sides as shown here. The U-shaped supports can generally be attached so that when the compression piston or suction cup is positioned over the sternum, the rotational angle with elevation of the U-shaped member is the same as the heart. However, in some embodiments, the support arm 408 may be more generally L-shaped, with only a single point of coupling with base 402. In some embodiments, the support arm 408 may be configured to expand and/or contract to adjust a height of the chest compression device 412 to accommodate individuals of different sizes.

It should be noted that the elevation devices/head up devices (HUD) could serve as a platform for additional CPR devices and aids. For example, an automatic external defibrillator could be attached to the HUD or embodied within it and share the same power source. Electrodes could be provided and attached rapidly to the patient once the patient is place on the HUD. Similarly, ECG monitoring, end tidal $CO_2$ monitoring, brain sensors, and the like could be co-located on the HUD. In addition, devices that facilitate the cooling of a patient could be co-located on the HUD to facilitate rapid cooling during and after CPR.

It should be further noted that during the performance of CPR the compression rate and depth and force applied to the chest might vary depending upon whether the patient is in the flat horizontal plane or whether the head and thorax are elevated. For example, CPR may be performed with compressions at a rate of 80/min using active compression-decompression CPR when flat but at 100 per minute with head and thorax elevation in order to maintain an adequate perfusion pressure to the brain when the head is elevated. Moreover, with head elevation there is better pulmonary circulation so the increase in circulation generated by the higher compression rates will have a beneficial effect on circulation and not "overload" the pulmonary circulation which could happen when the patient is in the flat horizontal plane.

Figure 5A:
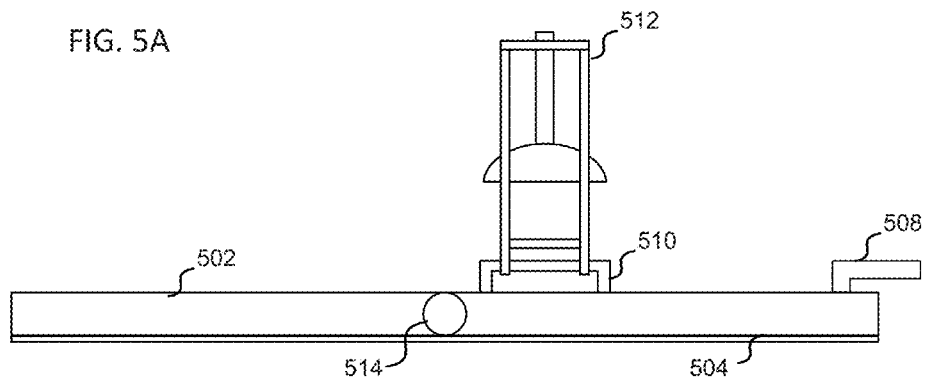
FIG. 5A depicts an elevation device in a stowed position according to embodiments.

FIGS. 5A-7C illustrate embodiments of simplified elevation devices according to the invention. Turning first to FIG. 5A, an elevation device 500 is shown in a stowed position. Elevation device 500 may be configured to be supported by a generally flat surface, such as a floor, the ground, a stretcher, a table, a bed, and/or other generally flat, supportive surface. The elevation device 500 may be configured to elevate the entire upper body of an individual, bending the individual at the waist. Elevation device 500 includes two support surfaces that are moveable relative to one another. A first support surface 502 may be generally aligned with a first plane and may be configured to support the individual's lower body at a position below the individual's waist. In some embodiments, the first support surface 502 may be entirely flat, and thus completely aligned with a first plane, while in other embodiments, the first support surface 502 may have a contoured profile that is largely, but not entirely, aligned with a single plane. The first plane may be aligned with a horizontal plane or at a slight angle (between about 0 and 5 degrees) above the horizontal plane. The first support surface 502 may be pivotally coupled with a second support surface 504 that is generally aligned with a second plane. The second support surface 504 may be similar to the upper supports described elsewhere herein. A pivot point 514 may couple the two support surfaces together at a position proximate an individual's waist. The second support surface 504 may be configured to be positioned under and to support the entirety of the individual's upper body, including the heart, shoulders, and head. The second support surface 504 is angularly positionable relative to the first support surface 502 such that an angle of the second plane may be adjusted. When pivoted, the second support surface 504 may be raised to elevated the individual's upper body as shown in FIG. 5B.

For example, the second support surface 504 may be pivoted between about 5 and 45 degrees above the first support surface 502 and/or the horizontal plane to sufficiently elevate the individual's head, shoulders, and heart relative to the rest of the patient's body.

In some embodiments, the first support surface 502 and/or the second support surface 506 may have a curved profile such that a medial section of the portion of the support surface is lower relative to end sections of the portion of the support surface. Such a profile may allow the support surface to more closely match the contour of an individual's back. Additionally, the curved profile may make the support surface flexible. This flexibility helps when the elevation device 500 is used in conjunction with a chest compression device, as the flexibility ensures that the right amount force applied to the patient's chest. For example, a central portion of the support surface may flex in the presence of excessive force, thereby acting as a flexible backplate to absorb some of the force. For example, as a plunger of a chest compression device is pressed into the patient's chest, some force is transmitted through the patient to the support surface. The support surface may be configured to bend away from the patient if this transferred force exceeds a threshold. This allows for the delivery of compression at the appropriate depth for patients with differing chest wall sizes and stiffness's. This helps prevent broken ribs and/or other injuries to the patient caused by too much force being applied to the patient's chest, as the flexing backplate, rather than the ribs or other body structures, absorbs a significant portion of the excess force. Such a design is particularly useful when the elevation device 500 is used in conjunction with a chest compression device 512 such as the Lucas device, sold by Physio-Control, Inc. and/or the Zoll AutoPulse. However, it will be appreciated that the flexible support surface may be used in conjunction with any of the embodiments of elevation devices described herein. It should be appreciated that the portion of the elevation device 500 under the heart and thorax could also contain force, pressure, impedance, and/or position sensors to provide feedback to the chest compression device 512, assuring the proper compression depth and force are delivered, even though the amounts needed to provide the proper CPR may differ from patient to patient and may change over time.

In some embodiments, a contact surface of the first support surface 502 and/or the second support surface 504 may be textured and/or coated with and/or formed from a non-slip material to help prevent the patient from sliding downward during elevation of the second support surface 504, thereby maintaining the patient in a desired treatment position. In some embodiments, a neck pad, head cradle, arm pit flaps, and/or other positioning aids may be included on the first support surface 502 and/or the second support surface 504 to both aid in properly positioning a patient on the elevation device 500 and to ensure that the patient remains in the correct treatment position throughout the elevation and lowering of the patient's upper body. For example, a neck pad may be provided that supports the individual's neck. The neck pad may be configured to support the individual's spine in a region of the individual's C7 and C8 vertebrae. Such positioning may help maintain the patient in the sniffing position to maintain the patient's airway in a proper position for endotracheal intubation. In such a position, the neck is flexed and the head extended, allowing for patient intubation, if necessary, and airway management. In some embodiments, a position and/or angle of the neck pad and/or a different head support, such as a head cradle or head support pad, may be adjustable. This allows for better airway management as well as better support of the patient's head, and allows the elevation device 500 to be usable with patients of various sizes and flexibility levels. For example, a patient with a particularly stiff neck may need to be positioned and/or supported differently than a patient having a neck with normal levels of flexibility. The neck pad and/or head support may be configured to raise and/or lower relative to the second support surface 504 to adjust the height of the patient's head and/or neck. For example, second support surface 504 may have an opening that is configured to receive the patient's head. The head support may be in the form of a cradle that is coupled with the second support surface 504 using cables, rods, and/or other supports. The supports may be extended and/or retracted to raise and/or lower the cradle. In other embodiments, the head support may include an inflatable pad that contacts a portion of the patient's head. The pad may be inflated to raise the head and deflated to lower the head.

Elevation device 500 may include one or more support mechanisms that are configured to maintain the second support surface at a desired elevation. For example, elevation device 500 may include one or more support posts 506 that are each configured to maintain the second support surface 504 at an elevated position relative to the first support surface 502. Each support post 506 may be in the form of a kickstand, such as a top board prop of a grand piano that maintains the top board in an open position or like a prop rod that holds an automobile hood open. The support post 506 may be extended or otherwise positioned upward in engagement with an underside of the second support surface 504 to maintain the second support surface 504 at a desired elevation. For example, an underside of the second support surface 504 may include one or more receptacles that are configured to receive and secure an end of the support post 506. In some embodiments, multiple receptacles may be provided at different positions on the underside of the second support surface 504 such that the support post 506 may be used to elevate the second support surface 504 at various heights/angles.

In some embodiments, support post 506 may be hinged. A hinged support post 506 may be lockable in an extended position that allows the second support surface 504 to be raised relative to the first support surface 502 and locked into place. As just one example, a hinge of the hinged support post 506 may be locked in a straight, extended position and/or may include a sleeve that may be positioned over the hinge to prevent the hinge from pivoting, thereby maintaining the second support surface 504 at a desired position. In other embodiments, the support post 506 may be a telescoping pole, such as a rod formed by a number of nesting rods of various diameters. Friction between the rods may act to maintain the second support surface at a desired height. In some embodiments, the telescoping pole may include a lock mechanism, such as a clamp or sleeve that prevents the telescoping pole from contracting under the weight of the individual's upper body.

Other support posts 506 may be in the form of pneumatic and/or hydraulic struts that utilize pressurized fluids to maintain the second support surface 504 at a desired elevation. Each of these support posts 506 may be disengaged to lower the second support surface 504. For example, one end of a gas strut may be positioned at a pivot point on a base of elevation device 500 while the other end is fixed to an underside of the second support surface 504. The strut may be extended or contracted as the elevation of the second support surface 504 changes.

Depending on the type of support post 506 used, the second support surface 504 may be lowered with or without downward force being applied by an operator of the elevation device 500. For example, if the support post 506 is in the form of a kickstand, once the kickstand is disengaged, the second support surface 504 may lower under the weight of the patient's head. In other embodiments, such as those using telescoping, pneumatic, and/or hydraulic support posts 506, the operator of the elevation device 500 may need to press down on the second support surface 504 to lower it. In some embodiments using pneumatic and/or hydraulic support posts 506, the second support surface 504 may be lowered by depressurizing the support post 506, such as by actuating a pressure relief valve.

To aid in the raising and lowering of the second support surface 504, the second support surface 504 may include one or more handles 508. For example, the handles 508 may be provided on one or more sides of the second support surface 504 and/or along a top edge of the second support surface 504. It will be appreciated that while described using manual means for elevation, elevation device 500 may be fitted with controllers, motors, threaded rods, lead screws, pneumatic and/or hydraulic actuators, motor driven telescopic rods, other elevation mechanisms, and/or combinations thereof. In some embodiments, the motors may be coupled with a controller or other computing device. The controller may communicate with one or more input devices such as a keypad. This allows a user to select an angle and/or height of the heart and/or head to be raised using the motor and/or other actuator. Additionally, the controller may be coupled with one or more sensors, such as flow and pressure sensors. Sensor inputs may be used to automatically control the motor and angle of the supports based on flow and pressure measurements. A type of CPR and/or ITP regulation may also be controlled using these and/or other sensor inputs. In some embodiments, the electro-mechanical lift mechanisms may include disengagement mechanisms that allow the elevation device 500 to be operated manually. This allows the elevation device 500 to be operable even if a power source for the electromechanical features is unavailable, such as when a battery is dead or when there is no power outlet or other power source available.

In some embodiments, the elevation device 500 may include elevation mechanisms that do not require a pivot point. As just one example, the support posts 506 may be raisable arms that are positioned underneath the second support surface 504 at a front and back of the second support surface 504. The front arms may raise slower and/or raise to a shorter height than the back arms, thus raising a back portion of the second support surface 504 to a higher elevation than a front portion.

Oftentimes, the first support surface 502 and/or the second support surface 504 include a mounting site 510 for a chest compression device 512. The mounting site 510 may allow a chest compression device 512 to be removably and/or permanently attached to the elevation device 500. The mounting site 510 may be positioned such that when coupled, the chest compression device 512 is disposed in alignment with the patient's heart and generally perpendicular (within about 5 degrees of perpendicular) with the patient's chest. In embodiments where the elevation device 500 is configured to elevate the entire upper body of a patient, the mounting site 510 may be on the second support surface 504. The chest compression device 512 may be configured to repeatedly compress the individual's chest using manual and/or electro-mechanical force. For example, the chest compression device 512 may include one or more handles that are operably coupled with a plunger. An operator of the chest compression device 512 may grasp the handles and apply downward force to the plunger to compress the patient's chest. In some embodiments, the chest compression device 512 may be an active compression/decompression device. For example, a suction cup, adhesive pad, and/or other fastening mechanism may be secured to the patient's chest. The operator may then pull up on the handle to lift the patient's chest, thereby actively decompressing the chest.

Automatic chest compression devices 512 may also be used. For example, automatic chest compression devices 512 may include a reciprocating plunger that may be actuated by a motor, solenoid, and/or other electro-mechanical actuator. In other embodiments, active decompression may be provided to the patient receiving CPR with a modified load distributing band device (e.g. modified Zoll Autopulse® band) by attaching a counter-force mechanism (e.g. a spring) between the load distributing band and the head up device or elevation device 500. Each time the band squeezes the chest, the spring, which is mechanically coupled to the anterior aspect of the band via an arch-like suspension means, is actively stretched. Each time the load distributing band relaxes, the spring recoils pulling the chest upward. The load distributing band may be modified such that between the band the anterior chest wall of the patient there is a means to adhere the band to the patient (e.g. suction cup or adhesive material). Thus, the load distributing band compresses the chest and stretches the spring, which is mounted on a suspension bracket over the patient's chest and attached to the head up device. It will be appreciated that the above chest compression devices are merely provided as examples, and that numerous variants may be contemplated in accordance with the present invention.

In some embodiments, the second support surface 504 may be slidable and/or otherwise expandable and contractible lengthwise during elevation of the patient's upper body to maintain the patient in a correct position and to assist in preventing the patient from curling forward during the elevation process. For example, the second support surface 504 may include multiple pieces that are slidable or otherwise movable relative to one another to expand and contract to maintain the patient in a desired position. This expansion and contraction may be particular useful in embodiments with automatic chest compression devices 512, as the expansion and/or contraction may be useful in ensuring that chest compressions are delivered at a proper position and angle relative to the patient's chest. In some embodiments, the second support structure 504 may include an upper section that is slidable along a support frame to permit the thorax to move freely upward and remain elongate, rather than contract, during the elevation process. For example, the upper section may be supported on rollers with minimal friction. As the head, neck, and/or shoulders are lifted, the upper section may slide away from the thoracic compression, which relieves a buildup of pressure on the thorax and minimizes thoracic compression and migration. In some embodiments, the second support surface 504 or a portion thereof may be spring biased in a contraction direction such that the only shifting or expansion of the upper section or other component of the second support surface 504 is due to forces from the individual as the individual is subject to thoracic shift. In other embodiments, the second support surface 504 may be coupled with the first support surface 502 using telescoping rods or supports. These supports may extend and contract to move and/or otherwise adjust a position of the second support surface 504 (and the patient's head) relative to the first support surface 502. It will be appreciated by those skilled in the art that other mechanisms may be incorporated to combat the effects of thoracic shift.

In some embodiments, intrathoracic pressure management may be used during the administration of chest compressions. For example, an impedance threshold device configured to interface with the individual's airway may be attached to and/or used in conjunction with the elevation device 500.

In one embodiment, a controller may adjust an actuation speed of a motor or other elevation mechanism to raise or lower an upper support surface of the elevation device within the necessary time frame. For example, medical personnel may set a desired elevation time, such as between about 2 and 30 seconds. The controller will then operate a motor or other elevation mechanism to slowly raise the second support surface 504 from a starting elevation angle to a final elevation angle over the selected time period. The controller may also instruct the elevation mechanism to quickly lower the upper support 404 within a desired timeframe, often between about 1 and 10 seconds. In some embodiments, the controller may receive data from one or more physiological sensors and use this data to determine rates and timing of elevation and lowering. For example, the patient on the elevation device 500 may be monitored using an electrocardiogram (ECG). The ECG may detect a stable heart rhythm even if the individual has no palpable pulse. Based on this detection of the stable heart rhythm, it may be determined to stop the performance of chest compressions and to promptly lower the second support surface 504. For example, once it is detected that the patient has a stable heart rhythm, the controller may alert medical personnel that chest compressions should be ceased, and may send a signal to the motor or other actuator to cause the second support surface to rapidly lower. In some embodiments, alerting medical personnel may involve producing a visual indicator, such as lighting up a light emitting diode (LED) or other light source and/or presenting a textual and/or image-based display on a screen of the elevation device 500. In one embodiment, upon detecting a stable heart rhythm, the controller may send a command to the automatic chest compression device 512 that causes the chest compression device 512 to stop the delivery of chest compressions and/or decompressions. In another embodiment, upon detecting the stable heart rhythm, the controller will alert medical personnel, who may then operate the elevation device 500 to lower the second support surface 504. It will be appreciated that other sensors may be used in conjunction with the elevation device 500 to determine: when to start and/or stop CPR, when to elevate and/or lower a patient's upper body, a degree of elevation of the patient's upper body, a rate of elevation or lowering of the patient's upper body, and/or other parameters of CPR and/or ITPR.

Figure 5B:
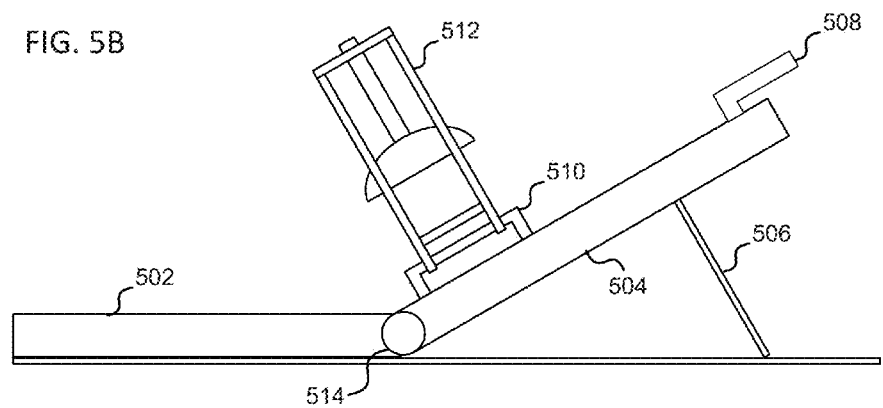
FIG. 5B depicts the elevation device of FIG. 5A in an elevated position according to embodiments.
Figure 6A:
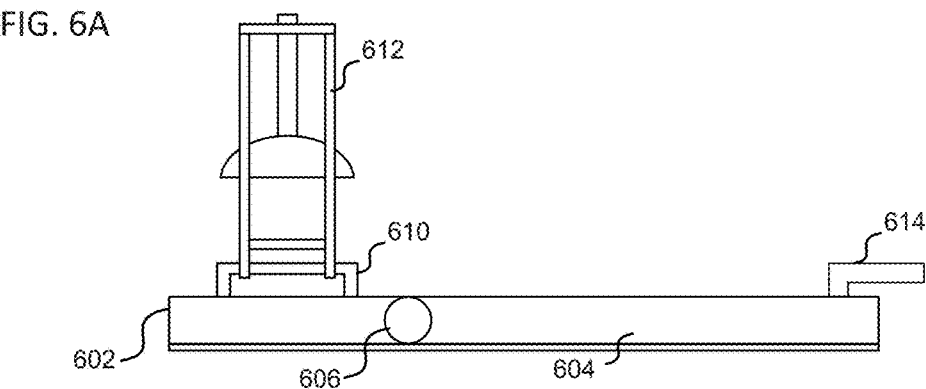
FIG. 6A depicts an elevation device in a stowed position according to embodiments.
Figure 6B:
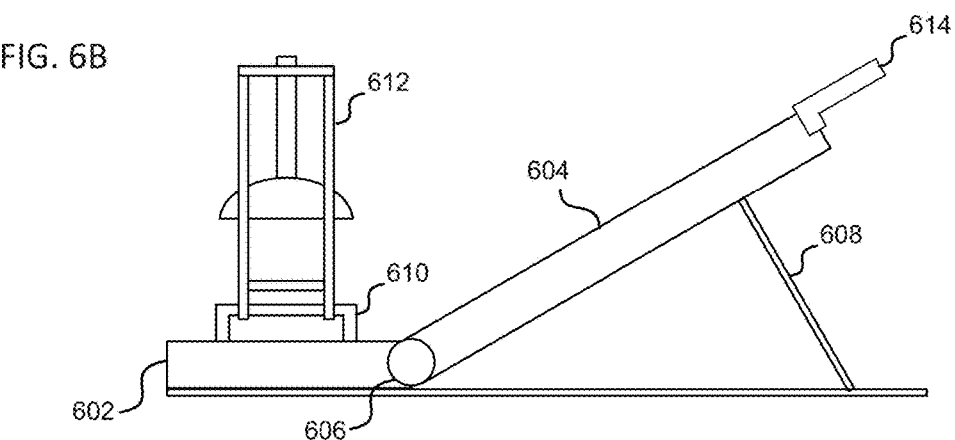
FIG. 6B depicts the elevation device of FIG. 6A in an elevated position according to embodiments.

In one embodiment shown in FIG. 6A, an elevation device 600 may be configured to elevate only a portion of the patient's upper body, including the upper chest/heart, shoulders, and head. Elevation device 600 is similar to elevation device 500 and may include similar features. Elevation device 600 includes a first support surface 602 that is configured to support at least a portion of the upper body, including the heart. Typically, the first support surface 602 extends below the individual's rib cage, and may extend to support all or a portion of the patient's lower body. In some embodiments, the first support surface 602 may be generally aligned with a horizontal plane, while in other embodiments, the first support surface 602 may be aligned with a plane that is angled slightly above horizontal, such as between about 1 and 5 degrees above horizontal. A second support surface 604 may be configured to support the individual's shoulders and head, with a pivot point 606 between the first support surface 602 and the second support surface 604 at a position proximate the individual's rib cage. The second support surface 604 may be pivoted relative to the first support surface 602 to raise the patient's shoulders and head as shown in FIG. 6B. Elevation device 600 may include one or more support posts 608, similar to those described in relation to FIGS. 5A and 5B, that are configured to maintain the second support surface 604 at a desired elevation. The elevation device 600 may also include a mounting site 610 for a chest compression device 612. The mounting site 610 is typically positioned on the second support surface 604 at a position in general alignment with the patient's heart. Elevation device 600 may also include one or more handles 614 to assist an operator in raising and/or lowering the second support surface. Elevation device 600 may also include one or more motors, controllers, and/or other lift mechanisms, similar to those described in relation to elevation device 500. These controllers and lift mechanisms may work in conjunction with the chest compression device 612 to raise and/or lower the patient's upper body and/or control a rate and/or timing of chest compressions as described in relation to FIGS. 5A and 5B.

Figure 7A:
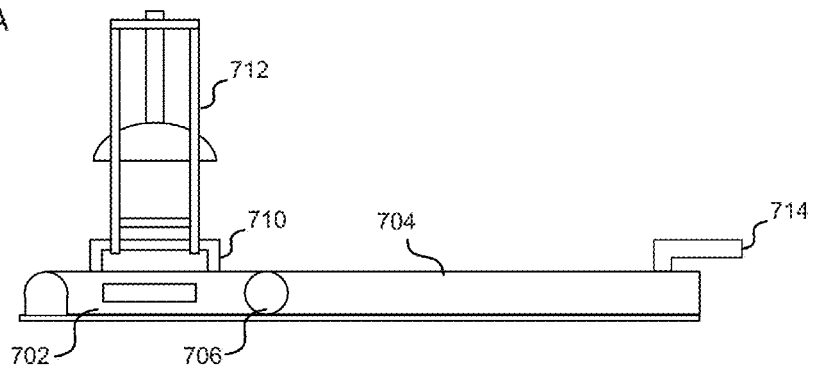
FIG. 7A depicts an elevation device in a stowed position according to embodiments.
Figure 7B:
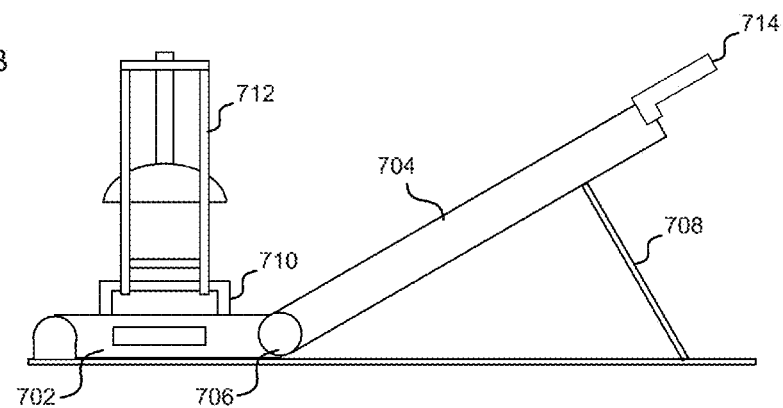
FIG. 7B depicts the elevation device of FIG. 7A in a partially elevated position according to embodiments.
Figure 7C:
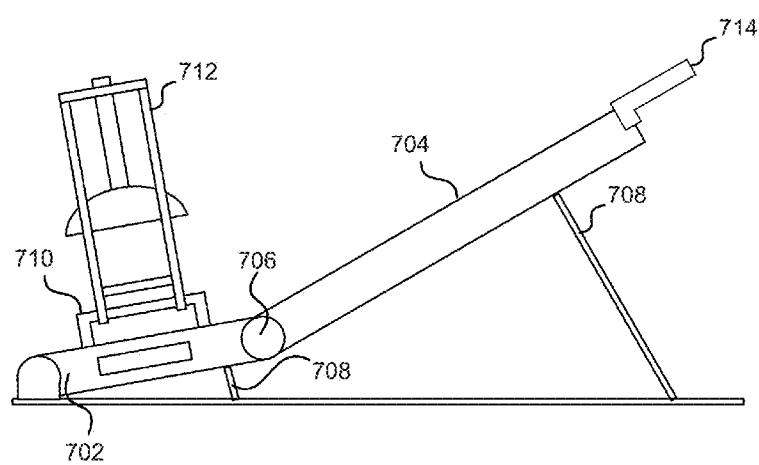
FIG. 7C depicts the elevation device of FIG. 7A in a fully elevated position according to embodiments.

In one embodiment shown in FIG. 7A, an elevation device 700 may be configured to elevate a portion of the patient's upper body, including the upper chest/heart, shoulders, and head. Elevation device 700 is similar to elevation devices 500 and 600 and may include similar features. Elevation device 700 includes a first support surface 702 that is configured to support at least a portion of the upper body. Typically, the first support surface 702 supports at least the patient's heart, similar to the thoracic plates described elsewhere herein. The first support surface 702 may be moved between a generally supine position and an elevated position, along with any angles therebetween. The generally supine position may involve the first support surface 702 being between about 0 and 10 degrees relative to a horizontal plane. The elevated position may have a maximum height of between about 4 cm and 15 cm. A second support surface 704 may be configured to support the individual's shoulders and head, with a pivot point 706 between the first support surface 702 and the second support surface 704 being disposed at a position just above the patient's heart. The second support surface 704 may be pivoted relative to the first support surface 702 to raise the patient's shoulders and head as shown in FIG. 7B. For example, the second support surface 704 may be raised to an angle of between about 15 and 45 degrees relative to horizontal while the first support surface 702 is left in the generally supine position. In some embodiments, both the first support surface 702 and the second support surface 704 may be elevated, such as shown in FIG. 7C. The first support surface 702 and the second support surface 704 may be elevated to the same or different angles, typically with the second support surface 704 being elevated at a larger angle relative to horizontal than the first support surface 702. In some embodiments, elevation device 700 may include a base (not shown) that is coupled with one or both of the first support surface 702 and the second support surface 704.

Elevation device 700 may include one or more support posts 708, similar to those described in relation to FIGS. 5A and 5B, that are configured to maintain the first support surface 702 and/or the second support surface 704 at a desired elevation. In some embodiments, the support posts 708 may be configured to rest upon a support surface, while in other embodiments, the support posts 708 extend between the base and the respective support surface. The elevation device 700 may also include a mounting site 710 for a chest compression device 712. The mounting site 710 is typically positioned on the first support surface 702 at a position in general alignment with the patient's heart. Elevation device 700 may also include one or more handles 714 on the first support surface 702 and/or the second support surface 704 to assist an operator in raising and/or lowering the respective support surface. Elevation device 700 may also include one or more motors, controllers, and/or other lift mechanisms, similar to those described in relation to elevation device 500. These controllers and lift mechanisms may work in conjunction with the chest compression device 712 to raise and/or lower the patient's upper body and/or control a rate and/or timing of chest compressions as described in relation to FIGS. 5A and 5B.

In some embodiments, the elevation devices described herein may be foldable for easy carrying. For example, the elevation devices may be configured to fold up, much like a briefcase, at or near the axis of rotation of the upper support such that the upper support may be brought in close proximity with the thoracic plate and/or base. In some embodiments, the upper support may be parallel or substantially parallel (such as within 10° of parallel) to the base. In some embodiments, an underside of the base and/or upper support may include a handle that allows the folded elevation device to be carried much like a briefcase. In other embodiments, rather than having a fixed handle, the elevation device may include one or more mounting features, such as clips or snaps, that allow a handle to be attached to the elevation device for transportation while in the folded state. In some embodiments, a lock mechanism or latch may be included to lock the elevation device in the folded and/or unfolded state. In some embodiments the foldable head and thorax elevation CPR device may be folded up in a briefcase and include an automated defibrillator, physiological sensors, and the like.

Figure 8A:
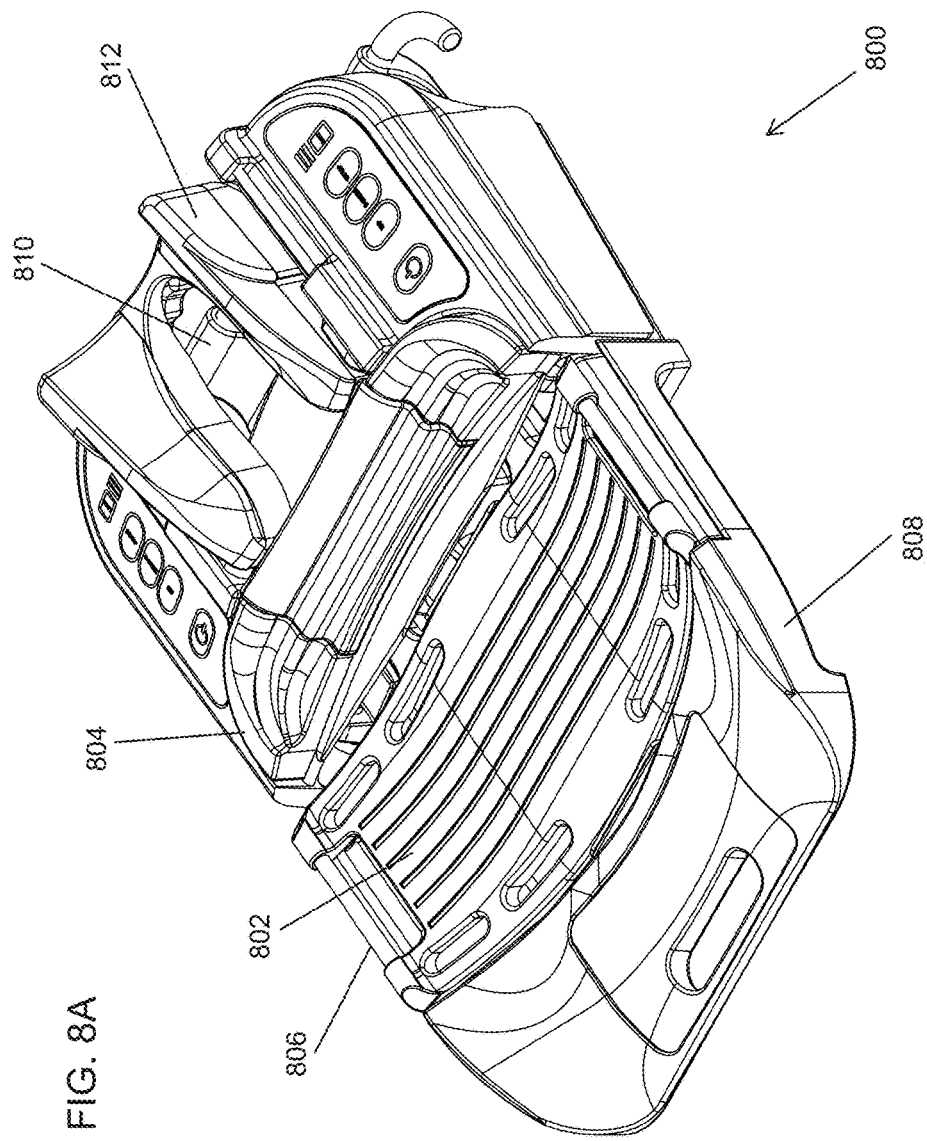
FIG. 8A depicts an isometric view of an elevation device with a head support according to embodiments.
Figure 8B:
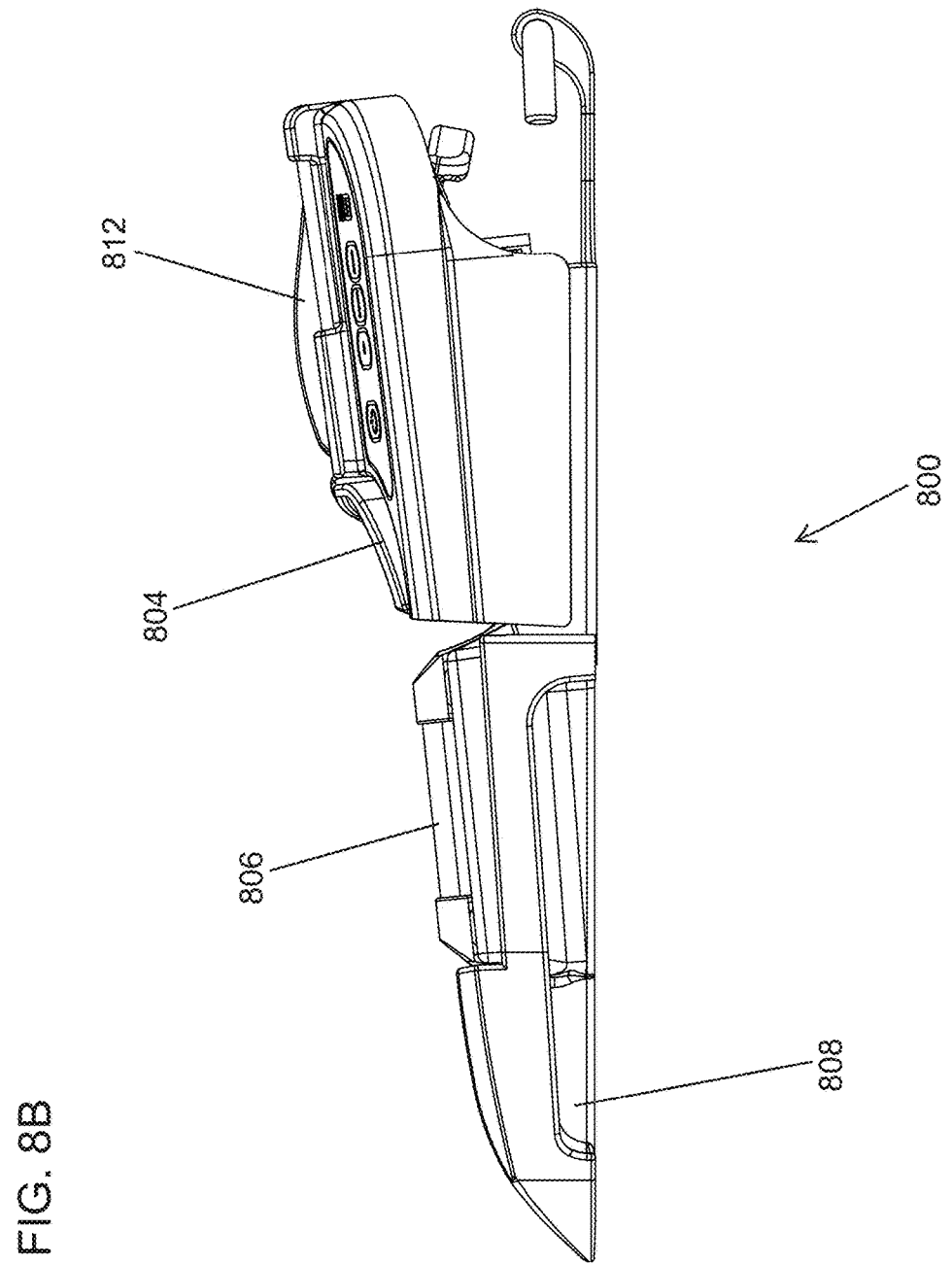
FIG. 8B depicts a side view of the elevation device of FIG. 8A with a lowered head support according to embodiments.

FIGS. 8A-8C depict an elevation device 800 that is similar to those described above. Turning to FIG. 8A, elevation device 800 includes a thoracic plate or first support surface 802 and an upper support or second support surface 804. The first support surface 802 may be configured to include one or more mounting supports 806 that are configured to secure a chest compression device (not shown) to the elevation device 800. In some embodiments, an angle of the first support surface 802 may be adjustable such that the first support surface 802 may be pivoted or otherwise moved to adjust an angle of both the first support surface 802 and the chest compression device. The second support surface 804 may be configured to elevate, such as by pivoting and/or otherwise raising the second support surface 804 relative to a base 808 of the elevation device 800 as described herein. In some embodiments, the elevation of the second support surface 804 may be mechanically coupled with the first support surface 802 such that a change in elevation of the second support surface 804 causes a corresponding change in angle of the first support surface 802. Oftentimes the corresponding change will result in the first support surface 802 being elevated to a lesser degree than the second support surface 804.

In some embodiments, the second support surface 804 may define an opening 810 that is configured to receive a portion of a patient's head. This opening 810 may help maintain the patient in the sniffing position for optimal airway management. Oftentimes, a head support 812 may be included on the second support surface 804. Here, head support 812 extends around a portion of the opening 810 to support at least a portion of the sides and/or top of the head. While shown extending partially around the opening 810, it will be appreciated that in some embodiments the head support 812 may extend around the entire opening 810. Head support 812 may be configured to be lowered and/or raised to adjust the position of the patient's head and/or to enable the elevation device 800 to be usable with patients of different sizes and flexibility levels. For example, as shown in FIG. 8B, head support 812 is shown in a lowered state. In some embodiments, the head support 812 may be inflatable and/or be expandable using one or more internal supports. To lower the head support 812, air or another fluid may be removed from a bladder of the head support 812. In embodiments with internal supports, such as support arms that form the profile of the head support 812, the internal supports may be retracted at least partially within the second support surface 804 to lower the head support 812. The head support 812 may also be raised as shown in FIG. 8C. In some embodiments, raising the head support 812 may include pumping air or another fluid into a bladder of the head support 812, causing the head support 812 to expand. In other embodiments, the head support 812 may be raised by extending one or more internal supports out of the second support surface 804 and into and interior of the head support 812. It will be appreciated that other mechanisms may be used to raise and/or lower a head support 812.

Figure 9:
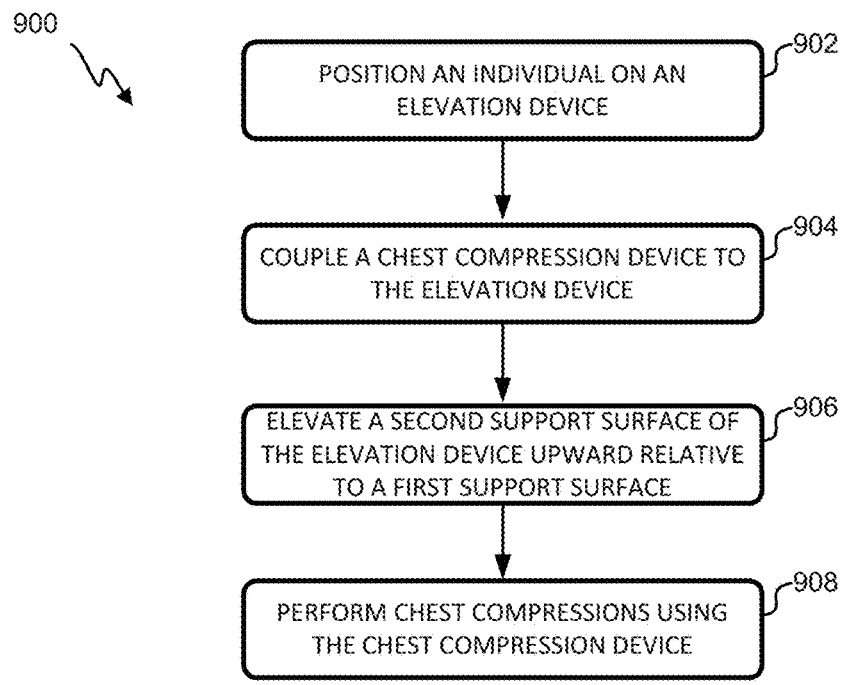
FIG. 9 is a flowchart of a process for elevated an individual during the performance of CPR according to embodiments.

FIG. 9 is a flowchart depicting a process 900 of elevating an individual during the performance of CPR. Process 900 may be performed using any of the elevation devices described herein. Process 900 may begin with positioning an individual on an elevation device at block 902. This may include positioning the individual's upper chest and heart such that they are supported by a first support surface that is generally aligned with a first plane. The individual's shoulders and head may be supported by a second support surface that is generally aligned with a second plane. In other embodiments, the individual's lower body may be supported by the first support surface, while the heart, upper chest, shoulders, and head are supported by the second support surface. The second support surface may be pivotally coupled with the first support surface. At block 904 a chest compression device may be coupled with at least one mounting site on the first support surface and/or the second support surface such that that the chest compression device is mounted just below the individual's armpits and in general alignment with the heart. The second support surface may be pivoted relative to the first support surface to raise the individual's shoulders and head relative to the heart at block 906. In some embodiments, this may be done by a user grasping the second support surface, such as by grasping a handle on the second support surface and pulling upward to raise the second support surface relative to the first support surface. At block 908 chest compressions may be performed using the chest compression device while the individual's shoulders and heart are raised relative to the heart. The chest compression device may be manual and/or automatic, and may be configured to compress and/or decompress the patient's chest.

In some embodiments, a decision to stop the performance of chest compressions and to promptly lower the head, heart and shoulders is based on sensing of a heart rhythm based on an electrocardiogram. For example, the patient may not have a discernable blood pressure or pulse, but may still have a regular heart rhythm that is detectable using an ECG. Such detection suggests the patient's heart may be pumping again, the head and shoulders are lowered, thereby making it easier for the heart to pump blood to the brain. After stopping the performance of chest compressions, the head, heart, and shoulders may be promptly lowered from the final elevation angle within a timeframe selected to prevent significant drainage of blood from the brain until the head, heart and shoulders are lowered. For example, the head, heart, and shoulders may be lowered within a clinically-desirable timeframe, oftentimes between about 1 and 10 seconds.

Figure 10:
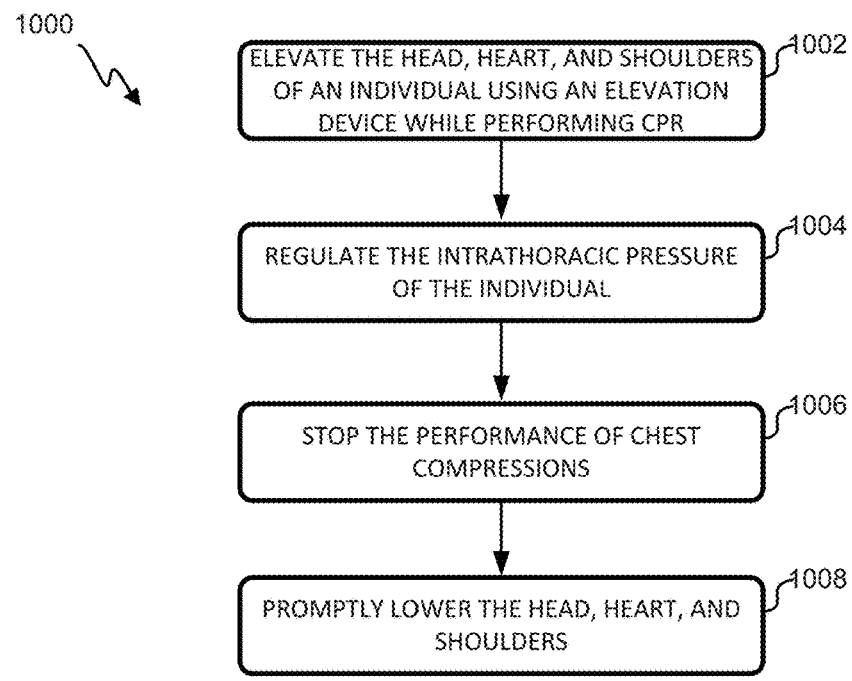
FIG. 10 is a flowchart of a process for elevated an individual during the performance of CPR according to embodiments.

FIG. 10 depicts a flowchart of a process 1000 for performing CPR. Process 1000 may be performed using any of the elevation devices described herein. Process 1000 may begin with elevating the head, heart, and shoulders of an individual from a starting elevation angle to a final elevation angle greater than zero degrees relative to horizontal while performing CPR by repeatedly compressing the chest at block 1002. The chest compressions may be performed manually and/or may be performed by a chest compression device. For example, a chest compression device, such as those described herein, may be positioned relative to the individual's chest and activated, causing the chest compression device to repeatedly compress the individual's chest. In some embodiments, the chest compression device may also be configured to actively decompress the individual's chest. For example, a portion of the chest compression device may be fastened to the individual's chest, such as using a suction cup, adhesive, and/or other fastening means. The chest compression device may then actively pull up on the patient's chest during a decompression stage of CPR.

In some embodiments, the elevation of the patient's head, heart and shoulders from the starting elevation angle to the final elevation angle is done over a period of between about 5 and 60 seconds. Such a time period ensures that sufficient time is provided to gradually pump the blood uphill to the brain while the head is being elevated to a final height. Oftentimes, the final elevation angle is between about 5 degrees to about 45 degrees relative to horizontal.

At block 1004, the intrathoracic pressure of the individual may be regulated while performing CPR. For example, an ITD may be interfaced with the patient's airway to regulate the patient's ITP. The performance of chest compressions may be stopped at block 1006. In some embodiments, a decision to stop the performance of chest compressions and to promptly lower the head, heart and shoulders is based on sensing of a stable heart rhythm based on an electrocardiogram. For example, the patient may not have a discernable blood pressure or pulse, but may still have a stable heart rhythm that is detectable using an ECG. Such detection ensures that as soon as the patient's heart is pumping again, the head and shoulders are lowered, thereby making it easier for the heart to pump blood to the brain.

After stopping the performance of chest compressions, the head, heart, and shoulders may be promptly lowered from the final elevation angle within a timeframe selected to prevent significant drainage of blood from the brain until the head, heart and shoulders are lowered at block 1008. For example, the head, heart, and shoulders may be lowered within a clinically-desirable timeframe of between about 1 and 10 seconds. In some embodiments, the head, heart and shoulders are lowered to an angle of between about zero degrees and 4 degrees relative to horizontal.

In some embodiments, the patient's intrathoracic pressure may be regulated, such as by using an impedance threshold device that is interfaced with the individual's airway.

Figure 11:
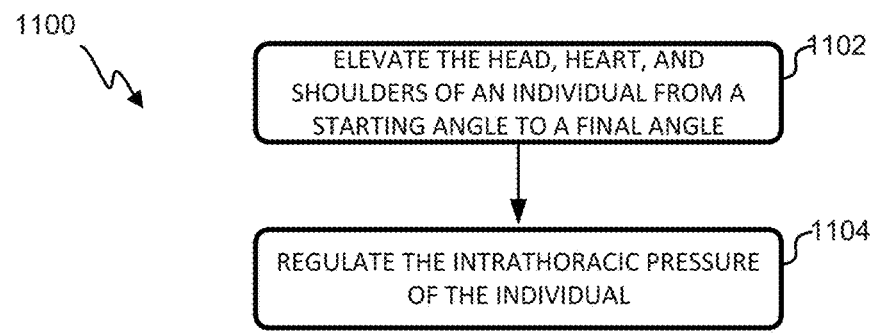
FIG. 11 is a flowchart of a process for elevated an individual during the performance of CPR according to embodiments.

FIG. 11 depicts a flowchart of another process 1100 for performing CPR. Process 1100 may involve the use of any of the elevation deices described herein. Process 1100 may begin with elevating the head, heart, and shoulders of an individual from a starting elevation angle to a final elevation angle greater than zero degrees relative to horizontal at block 1102. For example, the individual may be positioned on an elevation device such that at least the individual's head (and possible the heart and shoulders) is positioned on an upper support of the elevation device. The upper support may be pivoted upward relative to a base of the elevation device to elevate the individual's upper body to an angle of between about 0 and 45 degrees above a horizontal plane. In some embodiments, the individual's neck is supported on a neck pad of the elevation device such that the neck pad supports the individual's spine in a region of the individual's C7 and C8 vertebrae, which helps maintain the individual in the sniffing position. The upper support may be expandable lengthwise to maintain a position of the individual with the neck pad supporting the individual's spine in the region of the individual's C7 and C8 vertebrae. For example, during elevation of the upper support the individual's upper body causes the upper portion to extend away from the lower portion to assist in preventing the individual from curling forward. The elevation of the head, heart, and shoulders serves to actively drain venous blood from the brain using gravity while performing CPR by repeatedly compressing the chest. Elevation of the head, heart and shoulders assists to lower intracranial pressure and increase cerebral perfusion pressure during the performance of CPR.

The head, heart and shoulders may be elevated from the starting elevation angle to the final elevation angle within a timeframe selected to enable a sufficient amount of blood pressure to maintain an adequate amount of blood to the brain even though the brain is being elevated. Whether a sufficient amount of blood pressure is present to maintain an adequate amount of blood to the brain may be measure using several different techniques. As just one example, the cerebral perfusion pressure (CPP) of the patient may be monitored throughout the CPR process. A sufficient amount of blood to the brain may be provided when the CPP is greater than or equal to about 25% of baseline flow. The baseline flow may be specific to each individual patient and is based on the blood flow of that patient when they are not in cardiac arrest. In some embodiments, the 25% threshold of the baseline CPP may have a value of at least about 15 mm Hg. In some embodiments, the 25% threshold may have a value of at least about 0.2 ml/m/g of brain tissue.

In some embodiments, the timeframe may be between about 5 and 60 seconds. At block 1104, the intrathoracic pressure of the individual may be regulated while performing CPR with, for example, an impedance threshold device, to create a negative pressure within the chest during a relaxation phase of CPR. The active draining of venous blood from the brain using gravity in combination with the regulation of intrathoracic pressure while performing CPR also enhances a refilling of the heart with the increase of blood volume in the thorax, and reduces the magnitude of the venous pressure head that hits the brain with each compression to improve brain flow.

Process 1100 may also include stopping the performance of chest compressions and after stopping the performance of chest compressions, promptly lowering the head, heart and shoulders from the final elevation angle. This lowering may be done within a timeframe selected to prevent significant drainage of blood from the brain until the head, heart and shoulders are lowered. For example, the timeframe may be between about 1 and 10 seconds.

In some embodiments, process 1100 may include temporarily stopping the CPR procedure, positioning the patient in a horizontal plane or orientation, and assessing heart rhythm or another measured physiologic parameter of the patient to determine whether defibrillation is needed. This may be done using any number of methods and/or sensors. For example, an ECG or other physiologically-based signal may be used to determine whether the patient has a stable heart rhythm, and if not, the medical personnel may determine that defibrillation is necessary.

Figure 12:
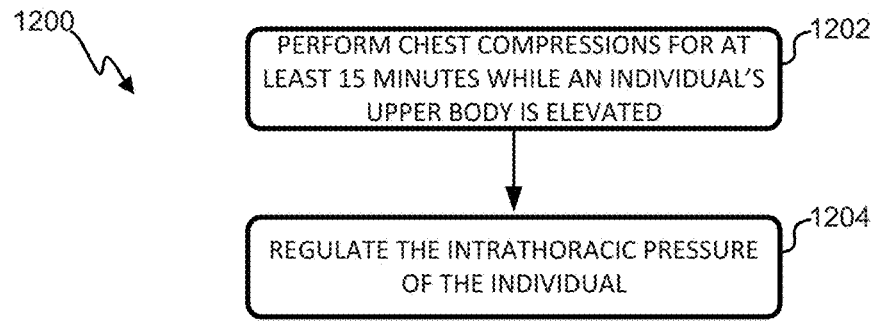
FIG. 12 is a flowchart of a process for doubling blood flow to the brain during the performance of CPR according to embodiments.

During prolonged CPR administration, the use of a combination of head up ACD CPR+ITD may significantly increase blood flow to the brain relative to supine standard CPR. FIG. 12 depicts such a process 1200. Process 1200 may be performed using any of the elevation devices described herein and may begin at block 1202 by performing chest compressions and decompressions on an individual for a period of at least 15 minutes using an active compression decompression CPR device or a load-distributing band CPR device while the head, shoulders, and heart are elevated. During the performance of CPR, the intrathoracic pressure of the individual may be regulated at block 1204, thereby doubling blood flow to the brain versus conventional CPR. In some embodiments, the intrathoracic pressure may be regulated using an ITD. The increase in brain blood flow is a direct result in the change in position of the head and thorax during CPR. This observation is likely due to the multiple effects of gravity and ACD CPR+ITD on intracranial and right heart pressures and trans-pulmonary blood flow. With HUP CPR, venous blood flow to the thorax and right heart is enhanced from the brain and paravertebral plexus; this decreases ICP and increases cardiac preload. This reduction in ICP lowers resistance to forward brain flow. The reduction in ICP and right-sided venous pressures in combination with the factor of pumping blood "uphill" with compression during HUP CPR also reduces the concussive forces that simultaneously strike the brain with each chest compression from a combination of simultaneous high arterial and venous high pressure waves. In these recent studies ACD CPR+ITD was used to generate high enough aortic pressures to overcome the challenge of pumping arterial blood "uphill". Without the ITD there was less of a clinically meaningful benefit with HUP CPR.

EXAMPLE 1

A recent study showed that head and thorax elevation during cardiopulmonary resuscitation improves cerebral perfusion in a swine model of prolonged of cardiac arrest. Most clinical CPR efforts last a minimum of 15-20 minutes. Prolonged cardiac arrest poses a potential risk when using a whole-body tilt approach to HUP CPR, since blood flow to the brain would be anticipated to decrease over time likely secondary to pooling of blood in the lower extremities. This physiology is well known from the use of head-up tilt-table testing to induce syncope. To reduce this potential risk, the use of elevation devices, such as those described herein that elevate just the head and upper thorax, demonstrated higher cerebral perfusion pressure (CerPP) in the HUP position over a period of 22 minutes with active compression decompression (ACD)+ITD CPR. With this device the head is elevated about 25 cm and the heart about 5 cm relative to the rest of the body. Building on prior studies, the hypothesis that CerPP and cerebral blood flow would be higher with HUP versus SUP during prolonged ACD CPR+ITD was tested. The primary endpoint of this study was brain blood flow after 15 minutes of CPR in a pig model of cardiac arrest secondary to ventricular fibrillation (VF). Secondary endpoints included blood flow after 5 minutes of CPR, systemic hemodynamics including intracranial pressure, and end tidal $CO_2$ ($ETCO_2$) for up to 20 minutes of CPR.

Methodology

Female Yorkshire farm pigs weighing between 36-44 kg were fasted overnight after acclimatizing in the animal care facility for at least three days. Intramuscular ketamine (10 mL of 100 mg/mL) was administered in the holding pen. Animals were then transferred to the surgical suite where they were treated with inhaled isoflurane at 1% to 2.5% for anesthesia. Animals were then intubated with a 7.5 French endotracheal tube and ventilation was performed using a ventilator (Narkomed, North American Drager, Telford, Pa.) with tidal volume 10 mL/kg. $ETCO_2$ and oxygen saturation were recorded with a CO2SMO Plus® (Novametrix Systems, Wallingford, Conn.). The respiratory rate and $FiO_2$ were adjusted to keep oxygen saturation above 92% and $ETCO_2$ between 37 and 43 mmHg. Intravenous (IV) access with an 18-gauge catheter was obtained through a lateral ear vein. All animals received room air temperature normal saline bolus of 1000 ml during preparatory phase to maintain the mean right atrial pressure between 4 and 7 mmHg. Temperature was monitored with an esophageal probe. Temperature was maintained between 36.5 and 38.5° C. using a warming blanket, as needed. Lead II electrocardiograms were continuously recorded. Proximal airway pressure, a surrogate for intrathoracic pressure, was measured with a differential pressure transducer (TSD160C, Biopac systems, Inc, Goleta, Calif.). Central aortic blood pressures were measured with a micromanometer-tipped catheter (Mikro-Tip Transducer, Millar Instruments, Houston, Tex.) placed through the right femoral artery into the descending thoracic aorta to the level of the diaphragm. A similar Millar catheter was placed in the right femoral vein and advanced to the right atrium (RA) to measure and monitor of right atrial pressure. A left femoral artery cannulation and a 7F pigtail catheter was positioned in the left ventricle (LV) under fluoroscopic guidance. This was used for the microsphere injections (see below). The position of all vascular micromanometer-tipped catheters was confirmed by fluoroscopy before the ventricular fibrillation was induced. Intracranial pressure (ICP) was measured by creating a burr hole in the skull, and then insertion of a Millar catheter into the parietal lobe as previously described. All animals received a 100 units/kg bolus of heparin intravenously every hour.

Data, including electrocardiographic monitoring, aortic pressure, RA pressure, LV pressure, ICP, and $ETCO_2$, was recorded continuously using the BioPac computer system (BioPac; BioPac Systems Inc, Goleta Calif.). All data was stored using the Biopac computer data analysis program. Arterial blood gases (ABG) were acquired through the femoral artery catheter and analyzed with a Gem Premier 3000 device (Instrumentation Laboratory, Lexington, Mass.).

When the preparatory phase was complete and the animal was hemodynamically stable, isoflurane was discontinued, and after 3 minutes ventricular fibrillation (VF) was induced with delivery of direct electrical current from a pacing wire placed in the right ventricle. ACD CPR+ITD was performed with an automatic piston device (Pneumatic Compression Controller; Ambu International, Glostrup, Denmark) as described previously. ACD CPR was performed at a rate of 80 compressions/min, with a 50% duty cycle and depth of 22.5% of antero-posterior chest diameter, and the chest was pulled upwards after each compression with a suction cup on the skin at a decompression force of approximately 10 kg. An ITD, (ResQPOD-16, Zoll Medical, Minneapolis, Minn.) was placed at the end of the endotracheal tube. The HUP CPR device used in this study elevated just the head and shoulders and upper thorax 30°, as previously described, such that the heart and head heights were ~5 and ~25 cm above the horizontal plane, respectively. While transitioning from supine to the HUP CPR was performed in an uninterrupted manner. During CPR, positive pressure ventilation was delivered with oxygen, titrated to a $SpO_2$ of >92%, with a tidal volume of 10 mL/kg. If the animal was noted to gasp during the resuscitation, time at first gasp was recorded. Succinylcholine was administered at a dose of 3 mg (0.075/kg) to inhibit gasping after the third gasp.

Microsphere Protocol

Blood flow to the heart, brain, kidney, and liver was measured with microsphere injection into the LV under stable baseline conditions 5 min prior to the induction of VF. Concurrently with the microsphere injections, reference blood samples were withdrawn continuously over 4 minutes from the descending aorta at a collection rate of 10 ml min$^{-1}$. Neutron activated microspheres (STERIspheres™, Bio-PAL™: BioPhysics Assay Laboratory, Worcester, Mass.) 15 microns in diameter containing Samarium (152Sm), Ytterbium (175Yb) and Lutetium (177Lu) were used. At the end of the procedure animals were sacrificed and then tissue samples from the posterior (pons portion of the brain-stem, hippocampus), left and right cortex), the heart (free left ventricle wall, apex, papillary muscle, and septum), the kidney (cortex), and the liver were obtained. Tissue and blood samples were desiccated and sent to the reference BioPhysics Assay Laboratory for analysis. Blood flow to the target organs was subsequently calculated after 5 and 15 min of CPR as described previously.

Experimental Protocol

Figure 13:
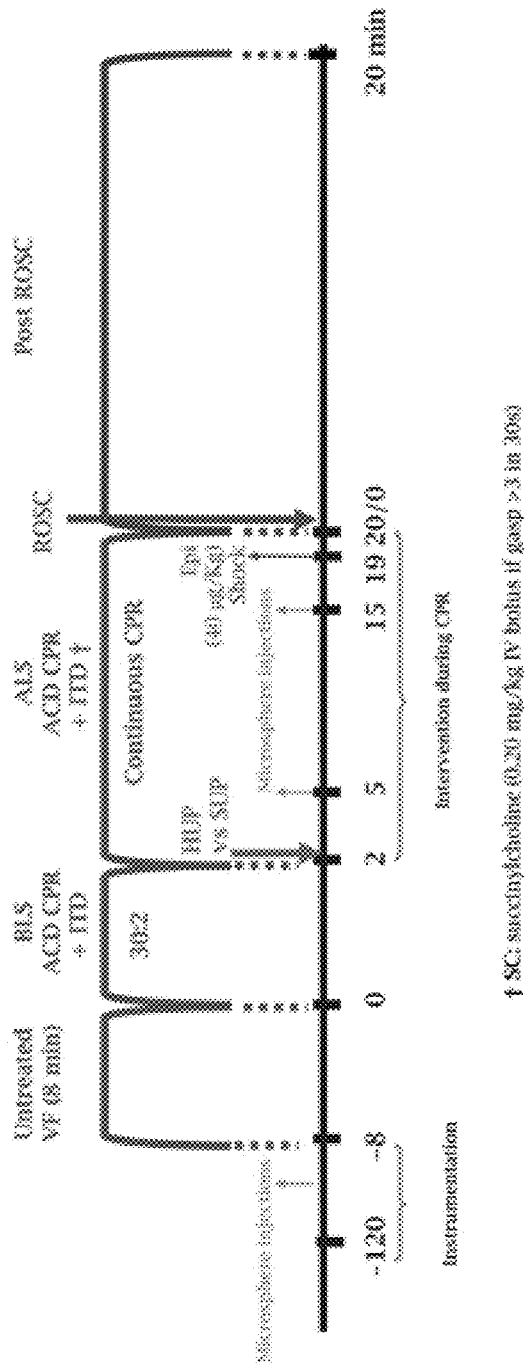
FIG. 13 is a flowchart depicting the experimental protocol of Example 1.

The experimental protocol is outlined in FIG. 13. After 8 minutes of untreated VF, ACD CPR+ITD was performed with a 30:2 compression: ventilation ratio, and positive pressure ventilation with room air was provided while all pigs were in the SUP to simulate basic life support (BLS). After 2 minutes of CPR, animals were randomized either HUP CPR or SUP CPR and continuous asynchronous ACD CPR+ITD CPR was continued for 18 minutes with a 10:1 compression: ventilation ratio to simulate advanced life support (ALS). Microsphere injections were performed after 5 and 15 minutes of CPR and 20 ml of blood were collected over 4 minutes (see above). After 19 total minutes of CPR, 0.5 mg of epinephrine was administered intravenously followed by 25 mg of amiodarone. One minute later, pigs were defibrillated with up to three 200 J biphasic shocks (X-series, Zoll Medical, Chelmsford Mass.). If return of spontaneous circulation (ROSC) was not obtained, CPR was resumed and a shock was delivered every 2 minutes together with 0.5 mg of epinephrine every 4 minutes. If spontaneous circulation was not restored after a total of 3 shocks, CPR was stopped. If ROSC was obtained, animals were euthanized with an intravenous injection of KCl 20 minutes later.

Data Analysis

The sample size calculation was based on previous studies. We estimated the brain blood flow would be approximately 25% higher in the HUP ACD CPR+ITD group. Assuming an alpha level of 0.05 and 80% power, 11 animals were needed per group to detect an 80% difference.

Hemodynamic data were analyzed at baseline just prior to the microsphere injection, and then after 5, 15, 19, and 20 minutes of CPR. Airway, aortic, right atrial, and intracranial pressures measurements were made from 3 sequential compression-decompression cycles between positive pressure breaths. These values were averaged for each of the compression-decompression cycle measurements for each time point in each animal study. The coronary perfusion pressure was calculated as the mathematical difference between the decompression phase aortic and right atrial pressures. In addition, when calculating the mean CerPP we used the mathematical difference between aortic and intracranial pressure over a 15 second interval at each time point.

Data are expressed as mean±standard deviation (SD). Statistical analysis was performed using SPSS 21 (IBM Corporation, USA). An unpaired Student's t-test was used to determine significance between HUP and SUP for the primary outcome of blood flow at 15 minutes, and also for secondary hemodynamic outcomes. A Fisher's exact test was used to compare ROSC rate. All statistical tests were two-sided, and a p value of less than 0.05 was required to reject the null hypothesis. Unadjusted p values are presented for the secondary analyses. Studies where technical difficulties were encountered due to either dislodgment of the left ventricular catheter, or inability to compress the chest 22.5% of the antero-posterior diameter, did not meet study inclusion criteria and were therefore not included in the results.

Results

Eighteen female pigs weighing 39.5±8.2 kg were randomized to CPR in HUP (n=8) or SUP (n=10). Results showing the blood flow to the brain, heart, kidney, and liver before VF and then 5 and 15 minutes after the start of CPR are provided in Table 1 reproduced below and illustrated in FIG. 14.

TABLE 1

Blood flow (ml/min/g) to various organs during cardiopulmonary resuscitation (CPR) in animals randomized to head and thorax elevation (HUP) and the whole body flat (SUP) positions. Values are presented as mean ± standard deviation; * p = 0.01 compared to the 15 min SUP CPR value.

| ml/min/g | Baseline | | 5 min CPR | | 15 min CPR | |
| --- | --- | --- | --- | --- | --- | --- |
| | SUP | HUP | SUP | HUP | SUP | HUP |
| n | 10 | 8 | 10 | 8 | 10 | 8 |
| Brain | 0.84 ± 0.17 | 0.86 ± 0.14 | 0.33 ± 0.06 | 0.45 ± 0.07 | 0.21 ± 0.04 | 0.42 ± 0.05 * |
| Heart | 1.37 ± 0.19 | 1.57 ± 0.17 | 0.51 ± 0.11 | 0.42 ± 0.09 | 0.33 ± 0.12 | 0.34 ± 0.06 |
| Kidney | 2.51 ± 0.29 | 2.32 ± 0.24 | 0.28 ± 0.08 | 0.38 ± 0.07 | 0.21 ± 0.06 | 0.31 ± 0.07 |
| Liver | 0.59 ± 0.11 | 0.76 ± 0.23 | 0.10 ± 0.02 | 0.08 ± 0.02 | 0.05 ± 0.02 | 0.08 ± 0.02 |

Figure 14:
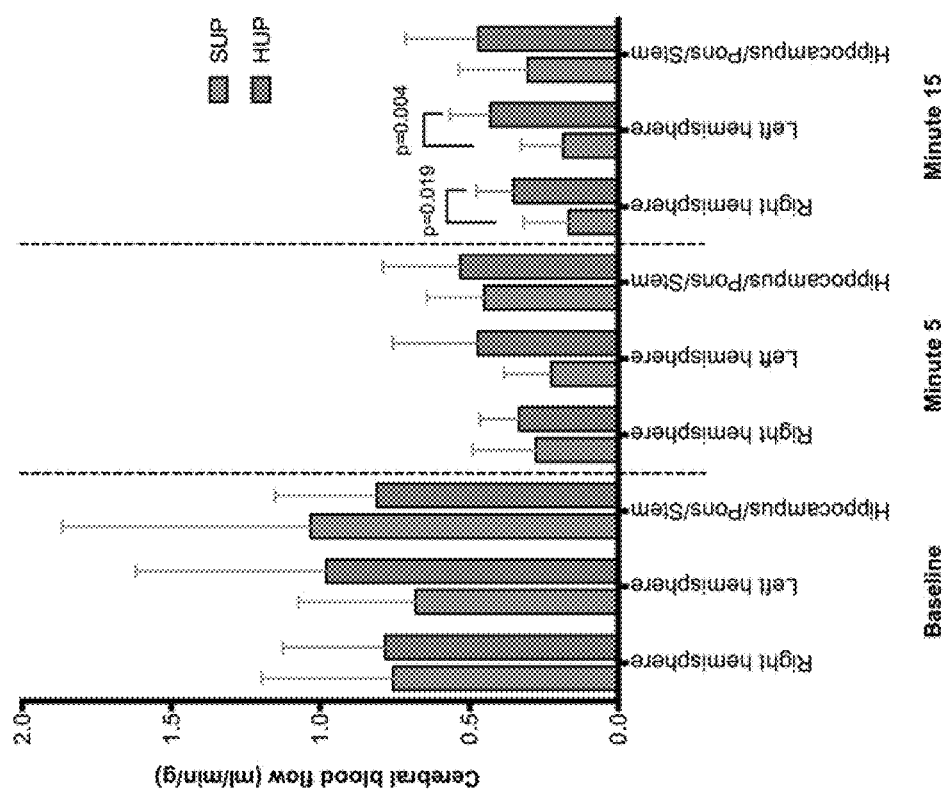
FIG. 14 is a chart depicting blood flow to the various areas of the brain with Head Up (HUP) and whole body flat (SUP) CPR according to Example 1.

The blood flow to the brain after 15 minutes of CPR, the primary study endpoint, was significantly higher in the HUP group at 0.42±0.05 ml/min/g versus 0.21±0.04 in the SUP group, respectively (p<0.01). When compared with pre-VF values, blood flow to the brain after 15 minutes of CPR was 25% of baseline in the SUP versus 50% in the HUP. Regional brain blood flow before cardiac arrest and after 5 and 15 minutes of HUP and SUP CPR are shown in FIG. 14.

Key hemodynamic variables for the two treatment groups are shown in Table 2 below.

TABLE 2

Hemodynamic measurements in animals randomized to the head up (HUP or supine (SUP) position during a prolonged cardiopulmonary resuscitation (CPR) effort. Values are presented as mean ± standard deviation. Abbreviations: Intrathoracic pressure (ITP), Aortic pressure (Ao), right atrial pressure (RA), intracranial pressure (ICP), Coronary Perfusion Pressure (CoPP), Cerebral Perfusion Pressure (CerPP), end-tidal CO2 (ETCO2), active compression decompression (ACD), impedance threshold device (ITD), * p ≤ 0.001;  p < 0.01; * p < 0.05, compared to the SUP CPR value at the same CPR time point.

| | N SUP = 10 HUP = 8 | | | | | |
| --- | --- | --- | --- | --- | --- | --- |
| | Baseline | | 5 min CPR | | 15 min CPR | |
| | SUP | HUP | SUP | HUP | SUP | HUP |
| ITP dia | 2.3 ± 1.2 | 2.0 ± 0.6 | −5.3 ± 3.0 | −5.8 ± 1.8 | −5.7 ± 2.8 | −6.0 ± 0.8 |
| Ao sys/dia | 96 ± 12/ 73 ± 10 | 86 ± 14/ 65 ± 13 | 56 ± 11/ 24 ± 5 | 58 ± 10/ 24 ± 5 | 53 ± 14/ 21 ± 6 | 59 ± 8/ 23 ± 4 |
| RA sys/dia | 7.4 ± 2.2/ 5.9 ± 2.3 | 7.1 ± 1.9/ 5.1 ± 1.7 | 60 ± 17/ 6.1 ± 4.9 | 49 ± 16/ 2.8 ± 3.6 | 52 ± 15/ 5.7 ± 4.2 | 48 ± 14/ 2.7 ± 3.4 |
| ICP mean | 18.8 ± 2.5 | 16.8 ± 3.6 | 18.3 ± 6.4 | 10.0 ± 7.0 * | 17.7 ± 5.5 | 7.7 ± 5.5 *** |
| CoPP dia | 66 ± 10 | 58 ± 13 | 18 ± 8 | 21 ± 6 | 15 ± 8 | 20 ± 5 |
| CerPP mean | 65 ± 11 | 60 ± 14 | 13 ± 7 | 26 ± 7 *** | 11 ± 9 | 28 ± 5 *** |
| $EtCO_2$ mean | 42 ± 2 | 42 ± 2 | 34 ± 16 | 40 ± 6 | 28 ± 15 | 32 ± 14 |

TABLE 2-continued

Hemodynamic measurements in animals randomized to the head up (HUP or supine
(SUP) position during a prolonged cardiopulmonary resuscitation (CPR) effort.
Values are presented as mean ± standard deviation. Abbreviations: Intrathoracic pressure (ITP),
Aortic pressure (Ao), right atrial pressure (RA), intracranial pressure (ICP), Coronary Perfusion
Pressure (CoPP), Cerebral Perfusion Pressure (CerPP), end-tidal CO2 (ETCO2), active compression
decompression (ACD), impedance threshold device (ITD), * p ≤ 0.001;  p < 0.01; * p < 0.05,
compared to the SUP CPR value at the same CPR time point.

| | N SUP = 10 HUP = 8 | | | |
|---|---|---|---|---|
| | 19 min CPR | | 20 min CPR | |
| | SUP | HUP | SUP | HUP |
| ITP dia | −5.6 ± 3.4 | −5.1 ± 1.5 | −5.1 ± 3.9 | −5.4 ± 1.3 |
| Ao sys/dia | 45 ± 17/ 16 ± 8 | 53 ± 9/ 20 ± 5 | 52 ± 22/ 21 ± 12 | 58 ± 13/ 23 ± 7 |
| RA sys/dia | 48 ± 14/ 5.1 ± 4.5 | 43 ± 14/ 2.0 ± 3.7 | 51 ± 11 6/6± | 46 ± 16/ 4 ± 5 |
| ICP mean | 15.7 ± 4.2 | 6.1 ± 5.1 *** | 14 ± 2 | 2 ± 2 *** |
| CoPP dia | 11 ± 11 | 18 ± 6 | 15 ± 15 | 20 ± 6 |
| CerPP mean | 8 ± 10 | 27 ± 5 *** | 6 ± 11 | 20 ± 7 ** |
| EtCO$_2$ mean | 24 ± 11 | 28 ± 12 | 23 ± 10 | 26 ± 11 |

Pigs treated with HUP CPR had significantly lower intracranial pressure (ICP) and higher CerPP after 5, 15, 19, and 20 minutes of ACD CPR+ITD versus SUP. One minute after epinephrine, the CerPP values remained higher in the HUP group. Another notable difference between the HUP and SUP groups was the time to first gasp. Time to first gasp was 282±51 seconds in the HUP group versus 437±185 seconds in the SUP group (p=0.045).

The ROSC rate and arterial blood gas values were similar between the two treatment groups. With HUP CPR 5/8 pigs achieved ROSC versus 3/10 in the SUP group (p=0.34). The arterial blood gases were similar at baseline and in the animals that had ROSC, as shown in Table 3 below.

TABLE 3

Arterial blood gases results of the Head Up (HUP) and Supine (SUP)
CPR groups. Values are presented as means ± standard deviation;
Abbreviations: Return of spontaneous circulation (ROSC), base
excess (BE).

| | Baseline | | ROSC | |
|---|---|---|---|---|
| | SUP | HUP | SUP (n-3) | HUP (n = 4) |
| pH | 7.46 ± 0.02 | 7.46 ± 0.03 | 7.02 ± 0.03 | 6.97 ± 0.03 |
| PaCO2 | 42 ± 3 | 44 ± 1 | 57 ± 5 | 73 ± 21 |
| PaO2 | 85 ± 10 | 93 ± 16 | 80 ± 10 | 91 ± 18 |
| HCO$_3^-$ | 30 ± 2 | 30 ± 1 | 15 ± 1 | 16 ± 4 |
| BE | 6 ± 3 | 6 ± 1 | −16 ± 1 | −10 ± 4 |
| SaO2 | 96 ± 2 | 97 ± 1 | 86 ± 5 | 83 ± 11 |

Discussion

The experimental protocol was designed to last 20 minutes, the average duration of many CPR efforts. The primary study endpoint was blood flow to the brain after 8 minutes of untreated VF and 15 minutes of CPR. ACD CPR+ITD was used based upon prior animal studies demonstrating that conventional CPR did not provide enough forward flow to pump blood "uphill" to the brain during HUP CPR, whereas a longer-term hemodynamic benefit was observed with HUP ACD+ITD CPR.

Results from the current study confirmed prior hemodynamic studies. The new results showed for the first time that blood flow can be maintained at levels of 50% of baseline values in this animal model of prolonged CPR. By contrast, ACD CPR+ITD in the flat position provided only 25% of normal brain flow after 8 minutes of untreated VF and 15 minutes of CPR. The microsphere blood flow studies parallel the hemodynamics findings of higher CerPP throughout the resuscitation effort. Two hemodynamic factors contributed to the higher and sustained CerPP in the HUP group; a gradual reduction in ICP in the HUP group over time and a sustained mean aortic pressure. By comparison, ICP remained relatively high and constant and aortic pressure relative low and constant in the SUP group. An earlier study demonstrated a similar improvement in CerPP, but such measurements are calculated by the difference between the arterial driving pressures and the resistance generated by ICP. This calculated CerPP has the potential to overestimate the actual delivery of blood to brain tissues as the arterial pressure cannot be easily measured in arterial of the brain, due to technical limitations. This limitation of the previous work highlighted the need to also demonstrate increased brain blood flow with HUP CPR in a prolonged CPR effort as shown in the current study.

Blood flow to the brain is needed to preserve and maintain brain function. Gasping is also dependent upon brain blood flow. Pigs treated with HUP CPR took their first spontaneous gasp earlier compared with the SUP group. This may be of clinical significance as gasping is associated with brain stem functionality and better clinical outcomes in patients in cardiac arrest. As such, time to first gasp may be a useful clinical endpoint when evaluating HUP CPR in human patients.

Previous studies have demonstrated that ACD CPR+ITD is superior to conventional CPR in terms of blood pressure, brain flow to the heart and brain, and long-term survival with favorable neurological function. In this study, ACD CPR+ITD in the SUP and HUP resulted in similar aortic pressures and arterial blood gases. Right atrial pressures tended to be lower in the HUP group but these differences were not statistically significant. The current study suggests that when ACD CPR+ITD is performed continuously, first in the SUP, during the transition from SUP to HUP, and then in the HUP for a prolonged period of time, that there is no increased risk of harm.

The study showed that after prolonged ACD CPR+ITD with elevation of the thorax and head, blood flow of the brain was 2-fold higher versus controls treated with the same method of CPR in the whole body flat position. These positive findings provide additional strong pre-clinical support to proceed with a clinical evaluation of elevation of the head and thorax during ACD CPR+ITD in humans in cardiac arrest. The increase in brain blood flow and quicker time to first gasp are direct results of the change in position of the head and thorax during CPR. These observations are likely due to the multiple effects of gravity and ACD CPR+ITD on intracranial and right heart pressures and trans-pulmonary blood flow. With HUP CPR, venous blood flow to the thorax and right heart is enhanced from the brain and paravertebral plexus; this decreases ICP and increases cardiac preload. This reduction in ICP lowers resistance to forward brain flow. The reduction in ICP and right-sided venous pressures in combination with the factor of pumping blood "uphill" with compression during HUP CPR also reduces the concussive forces that simultaneously strike the brain with each chest compression from a combination of simultaneous high arterial and venous high pressure waves. In these recent studies ACD CPR+ITD was used to generate high enough aortic pressures to overcome the challenge of pumping arterial blood "uphill". Without the ITD there was less of a clinically meaningful benefit with HUP CPR.

Specific details are given in the description to provide a thorough understanding of example configurations (including implementations). However, configurations may be practiced without these specific details. For example, well-known processes, structures, and techniques have been shown without unnecessary detail in order to avoid obscuring the configurations. This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the spirit or scope of the disclosure. Additionally, features described in relation to one embodiment may be incorporated into other embodiments while staying within the scope of the disclosure.

Also, configurations may be described as a process that is depicted as a flow diagram or block diagram. Although each may describe the operations as a sequential process, many of the operations may be performed in parallel or concurrently. In addition, the order of the operations may be rearranged. A process may have additional steps not included in the figure.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A method for performing cardiopulmonary resuscitation (CPR), comprising:
    performing CPR by repeatedly compressing the chest while gradually elevating the head, heart and shoulders of an individual from a starting elevation angle to a final elevation angle greater than zero degrees relative to horizontal;
    regulating the intrathoracic pressure of the individual while performing the CPR; and
    after stopping the performance of chest compressions, promptly lowering the head, heart, and shoulders from the final elevation angle within a clinically-desirable timeframe selected to prevent significant reduction in brain blood flow until the head, heart and shoulders are lowered,
    wherein the clinically-desirable timeframe is between about 1 and 60 seconds.

2. The method for performing cardiopulmonary resuscitation (CPR) of claim 1, wherein:
    the clinically-desirable timeframe is between about 1 and 10 seconds.

3. The method for performing cardiopulmonary resuscitation (CPR) of claim 1, wherein:
    the head, heart and shoulders are lowered to an angle of between about zero degrees and 4 degrees relative to horizontal.

4. The method for performing cardiopulmonary resuscitation (CPR) of claim 1, wherein:
    a decision to promptly lower the head, heart and shoulders is based on sensing of a physiological parameter.

5. The method for performing cardiopulmonary resuscitation (CPR) of claim 1, wherein:
    elevating the head, heart and shoulders comprises raising the head, heart and shoulders from the starting elevation angle to the final elevation angle over a period of between about 5 and 60 seconds.

6. The method for performing cardiopulmonary resuscitation (CPR) of claim 1, wherein:
    regulating the intrathoracic pressure is performed by an impedance threshold device that is interfaced with the individual's airway.

7. The method for performing cardiopulmonary resuscitation (CPR) of claim 1, further comprising:
    positioning the individual on an elevation device such that at least the individual's head is positioned on an upper support of the elevation device, wherein elevating the individual's head, heart and shoulders comprises pivoting the upper support upward relative to a base of the elevation device.

8. The method for performing cardiopulmonary resuscitation (CPR) of claim 1, wherein:
    the head, heart or shoulders of the individual are elevated to a final elevation angle between about fifteen degrees to about thirty degrees relative to horizontal.

9. The method for performing cardiopulmonary resuscitation (CPR) of claim 1, further comprising:
    positioning a chest compression device relative to the individual's chest; and
    activating the chest compression device to repeatedly compress the individual's chest.

10. The method for performing cardiopulmonary resuscitation (CPR) of claim 9, further comprising:
    actively decompressing the individual's chest using the chest compression device.

11. The method for performing cardiopulmonary resuscitation (CPR) of claim 1, wherein: the head, heart, and shoulders are promptly lowered when the patient has no significant blood pressure.

12. A method for performing cardiopulmonary resuscitation (CPR), comprising:

performing CPR by repeatedly compressing the chest while gradually elevating the head, heart and shoulders of an individual from a starting elevation angle to a final elevation angle greater than zero degrees relative to horizontal to actively drain venous blood from the brain using gravity, whereby elevation of the head, heart and shoulders assists to lower intracranial pressure and increase cerebral perfusion pressure during the performance of the CPR, wherein the head, heart and shoulders are elevated from the starting elevation angle to the final elevation angle within a clinically-desirable timeframe selected to enable enough blood flow to the brain even though the brain is being elevated;

regulating the intrathoracic pressure of the individual while performing CPR to create a negative pressure within the chest during a relaxation phase of CPR; and after stopping the performance of chest compressions, promptly lowering the head, heart and shoulders from the final elevation angle within a lowering timeframe selected to prevent significant drainage of blood from the brain until the head, heart and shoulders are lowered;

wherein the lowering timeframe is between about 1 and 60 seconds.

13. The method for performing cardiopulmonary resuscitation (CPR) of claim 12, wherein:
the clinically-desirable timeframe is between about 2 and 60 seconds.

14. The method for performing cardiopulmonary resuscitation (CPR) of claim 12, further comprising:
temporarily stopping the CPR procedure;
positioning the patient in a horizontal plane or orientation; and
assessing heart rhythm or another measured physiologic parameter of the patient to determine whether one or both of more CPR or defibrillation are needed.

15. The method for performing cardiopulmonary resuscitation (CPR) of claim 12, wherein:
active draining of venous blood from the brain using gravity in combination with the regulation of intrathoracic pressure while performing CPR also enhances a refilling of the heart with the increase of blood volume in the thorax, and reduces the magnitude of the venous pressure head that hits the brain with each compression to improve brain flow.

16. The method for performing cardiopulmonary resuscitation (CPR) of claim 12, further comprising:
positioning the individual on an elevation device such that at least the individual's head is positioned on an upper support of the elevation device, wherein elevating the individual's head, heart and shoulders comprises pivoting the upper support upward relative to a base of the elevation device.

17. The method for performing cardiopulmonary resuscitation (CPR) of claim 16, wherein:
the individual's neck is supported on a neck pad of the elevation device such that the neck pad supports the individual's spine in a region of the individual's C7 and C8 vertebrae; and
the method further comprises expanding the upper support lengthwise to maintain a position of the individual with the neck pad supporting the individual's spine in the region of the individual's C7 and C8 vertebrae, wherein during elevation of the upper support the individual's upper body causes the upper portion to extend away from the lower portion to assist in preventing the individual from curling forward.

* * * * *